(12) United States Patent
Takaku et al.

(10) Patent No.: US 9,711,733 B2
(45) Date of Patent: Jul. 18, 2017

(54) ORGANIC THIN FILM TRANSISTOR, ORGANIC SEMICONDUCTOR THIN FILM, AND ORGANIC SEMICONDUCTOR MATERIAL

(71) Applicant: FUJIFILM Corporation, Tokyo (JP)

(72) Inventors: Koji Takaku, Kanagawa (JP); Yasunori Yonekuta, Kanagawa (JP); Wataru Sotoyama, Kanagawa (JP); Masaru Kinoshita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/816,517

(22) Filed: Aug. 3, 2015

(65) Prior Publication Data
US 2015/0340624 A1 Nov. 26, 2015

Related U.S. Application Data

(63) Continuation of application No. PCT/JP2014/052218, filed on Jan. 31, 2014.

(30) Foreign Application Priority Data

Feb. 4, 2013 (JP) .................. 2013-019583
Jan. 30, 2014 (JP) .................. 2014-015378

(51) Int. Cl.
| | | |
|---|---|---|
| C07D 277/60 | (2006.01) |
| C07D 417/00 | (2006.01) |
| C07D 277/84 | (2006.01) |
| C07D 209/76 | (2006.01) |
| C08K 5/34 | (2006.01) |
| C08K 5/48 | (2006.01) |
| H01L 51/00 | (2006.01) |
| C07F 7/18 | (2006.01) |
| C08K 5/47 | (2006.01) |
| C09D 125/06 | (2006.01) |
| C08J 5/18 | (2006.01) |
| C07D 498/04 | (2006.01) |
| C07D 513/04 | (2006.01) |
| C07F 7/08 | (2006.01) |
| C09D 125/16 | (2006.01) |
| H01L 51/05 | (2006.01) |

(52) U.S. Cl.
CPC ........ *H01L 51/0071* (2013.01); *C07D 498/04* (2013.01); *C07D 513/04* (2013.01); *C07F 7/0849* (2013.01); *C07F 7/184* (2013.01); *C08J 5/18* (2013.01); *C08K 5/47* (2013.01); *C09D 125/06* (2013.01); *C09D 125/16* (2013.01); *H01L 51/0035* (2013.01); *H01L 51/0065* (2013.01); *H01L 51/0068* (2013.01); *H01L 51/0094* (2013.01); *C08J 2325/06* (2013.01); *H01L 51/0541* (2013.01); *H01L 51/0545* (2013.01); *H01L 51/0558* (2013.01)

(58) Field of Classification Search
None
See application file for complete search history.

(56) References Cited

FOREIGN PATENT DOCUMENTS

| | | |
|---|---|---|
| JP | 48-41118 | 12/1973 |
| JP | 05-214335 A | 8/1993 |

OTHER PUBLICATIONS

Sho et al. Machine translation of JP 48-41118, p. 1-9.*
An Office Action; "Notification of Reasons for Refusal" issued by the Japanese Patent Office on Jul. 12, 2016, which corresponds to Japanese Patent Application No. 2014-015378 and is related to U.S. Appl. No. 14/816,517; with English language translation.
Notification of Transmittal of Translation of the International Preliminary Report on Patentability and Translation of Written Opinion of the International Searching Authority; PCT/JP2014/052218 issued on Aug. 13, 2015.
International Search Report and Written Opinion for application No. PCT/JP2014/052218 dated Mar. 25, 2014.
Erdmann, Kolbe, Meyer, Rossow and Staudinger, Journal Fur Praktische Chemie, Feb. 7, 1963.
An Office Action issued by the Taiwanese Patent Office on Apr. 24, 2017, which corresponds to Taiwanese Patent Application No. 103103790 and is related to U.S. Appl. No. 14/816,517; with English language excerption.

* cited by examiner

*Primary Examiner* — Susannah Chung
*Assistant Examiner* — Robert T Butcher
(74) *Attorney, Agent, or Firm* — Studebaker & Brackett PC

(57) ABSTRACT

An organic thin film transistor containing a compound represented by one of the following formulae in a semiconductor active layer has a high carrier mobility and a small change in the threshold voltage after repeated driving. X represents S or O, and at least one of $R^1$ to $R^6$ represents -L-R wherein L represents alkylene, etc., and R represents alkyl, etc.

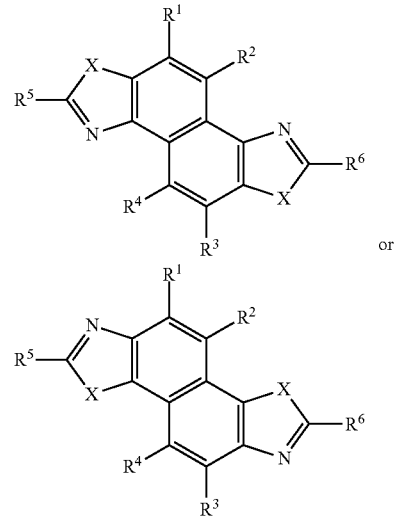

24 Claims, 2 Drawing Sheets

ORGANIC THIN FILM TRANSISTOR, ORGANIC SEMICONDUCTOR THIN FILM, AND ORGANIC SEMICONDUCTOR MATERIAL

CROSS-REFERENCE TO RELATED APPLICATIONS

This application is a Continuation of PCT International Application No. PCT/JP2014/052218 filed on Jan. 31, 2014, which claims priority under 35 U. S. C. Section 119(a) to Japanese Patent Application No. 2013-019583 filed on Feb. 4, 2013, and Japanese Patent Application No. 2014-015378 filed on Jan. 30, 2014. Each of the above applications is hereby expressly incorporated by reference, in its entirety, into the present application.

BACKGROUND OF THE INVENTION

Field of the Invention

The present invention relates to an organic thin film transistor, an organic semiconductor thin film, and an organic semiconductor material. More specifically, the invention relates to a compound having a naphthothiazole or naphthoxazole structure, an organic thin film transistor containing the compound, an organic semiconductor material for a non-light emitting organic semiconductor device containing the compound, a material for an organic thin film transistor containing the compound, a coating solution for a non-light emitting organic semiconductor device containing the compound, and an organic semiconductor thin film for a non-light emitting organic semiconductor device containing the compound.

Background Art

A device using an organic semiconductor material is expected to have various advantages as compared to an ordinary device using an inorganic semiconductor material, such as silicon, and thus is receiving much attention. Examples of the device using an organic semiconductor material include a photoelectric conversion device, such as an organic thin film solar cell and a solid state image sensing device, using an organic semiconductor material as a photoelectric conversion material, and a non-light emitting organic transistor. The device using an organic semiconductor material has a possibility that a device having a large area may be produced at a low temperature and a low cost, as compared to a device using an inorganic semiconductor material. Furthermore, the characteristics of the material may be easily changed by changing the molecular structure thereof, and thus there is a wide range of variations in materials, by which functions and devices that have not been achieved by an inorganic semiconductor material may be realized.

For example, Patent Document 1 describes a compound having a naphthoxazole structure and having as a substituent thereof an unsubstituted phenyl group, a phenyl-substituted phenyl group or a phenyl-substituted ethenyl group, and describes that the use thereof as a fluorescent material of organic electroluminescence (which may be referred to as organic EL or organic electroluminescence) may provide an electroluminescent device that maintains the light emission capability thereof for a prolonged period of time and has excellent durability. However, Patent Document 1 does not describe the use of the compound having such a structure in an organic thin film transistor.

On the other hand, there have been cases of using a compound having naphthothiazole or naphthoxazole in fields that have no relationship to the field of an organic semiconductor. For example, Patent Document 2 describes a method of dyeing a polymer compound with a naphthoxazole fluorescent whitening agent, and describes that a polymer compound may be optically whitened in a graceful manner. Patent Document 2 also does not describe the use of the compound having such a structure in an organic thin film transistor and other organic semiconductors.

Non-patent Documents 1 to 3 describe a compound having a naphthothiazole or naphthoxazole structure and having as a substituent thereof a methyl group, an ethyl group or a methylamino group, and describe the use thereof as an intermediate for a cyanine dye. However, Non-patent Documents 1 to 3 do not describe the use of the compound having such a structure in an organic thin film transistor.

CITATION LIST

Patent Documents

Patent Document 1: JP-A-05-214335
Patent Document 2: JP-B-48-041118

Non-Patent Documents

Non-patent Document 1: Ukrains'kii Khemichnii Zhurnal, 22, 772 (1956)
Non-patent Document 2: Journal of the Chemical Society [Section] C: Organic, (21), 2212-20 (1967)
Non-patent Document 3: Journal fuer Praktische Chemie (Leipzig), 18, 292-6 (1962)

SUMMARY OF INVENTION

It has been known that a polycyclic condensed compound containing an aromatic heterocyclic ring is useful as a material for an organic EL device, as described in Patent Document 1. However, it may not be said that a compound that is useful as a material for an organic EL device is immediately useful as a semiconductor material for an organic thin film transistor. This is because there is a difference in the characteristics demanded for the organic compound between an organic EL device and an organic thin film transistor. An organic EL device generally requires charge transport in the thickness direction of the thin film (which is generally from several nanometers to several hundred nanometers), whereas an organic thin film transistor requires charge (carrier) transport in a long distance between electrodes in the plane direction of the thin film (which is generally from several micrometers to several hundred micrometers). Accordingly, the demanded carrier mobility is considerably high. Thus, as a semiconductor material for an organic thin film transistor, an organic compound that has a high alignment order of molecules with high crystallinity is demanded. Furthermore, for achieving a high carrier mobility, the π-conjugate plane is preferably perpendicular to the substrate. In an organic EL device, on the other hand, a device that has a high light emission efficiency and uniform in-plane light emission is demanded for enhancing the light emission efficiency. In general, an organic compound having high crystallinity may be a cause of light emission defects, such as in-plane electric field unevenness, in-plane light emission unevenness and light emission quenching, and thus the material for an organic EL device is demanded to have high amorphous property with low crystallinity. Accordingly, even when an organic compound constituting a material for an organic EL device is diverted to an organic semiconductor material, good transistor characteristics may not immediately obtained.

For example, the present inventors actually apply the compound having a naphthoxazole structure and having as a substituent thereof an unsubstituted phenyl group, a phenyl-substituted phenyl group or a phenyl-substituted ethenyl group applied to an organic EL device in Patent Document 1 to an organic thin film transistor, but it has been found that there is a problem that sufficient transistor characteristics are not obtained. Specifically, in the case where the compounds that are described with specific structures thereof in Patent Document 1 are applied as an organic semiconductor material to an organic thin film transistor, the investigations made by the inventors reveal that a high carrier mobility is not obtained, and the change in the threshold voltage becomes large in repeated driving. The large change in the threshold voltage brings about a problem that the transistor is deteriorated in reliability and may not be used for a prolonged period of time. The change in the threshold voltage after repeated driving is a problem that has not been known in the art.

Under the circumstances, the inventors have made investigations for solving the problems in the related art. An object to be achieved by the invention is to provide an organic thin film transistor that has a high carrier mobility and a small change in the threshold voltage after repeated driving.

As a result of earnest investigations for solving the problems, the inventors have found that an organic thin film that is advantageous for carrier transport may be obtained by introducing a substituent that has the particular structure and the suitable length and is capable of promoting the molecular orientation, into a compound having a naphthothiazole or naphthoxazole structure. Furthermore, the inventors have found that an organic thin film transistor that uses the naphthothiazole or naphthoxazole derivative having the structure in a semiconductor active layer shows a small change in the threshold voltage after repeated driving, and thus have completed the invention.

The invention as a specific measure for solving the problems includes the following aspects.

(1) An organic thin film transistor containing a compound represented by the following formula (1-1) or (1-2) in a semiconductor active layer:

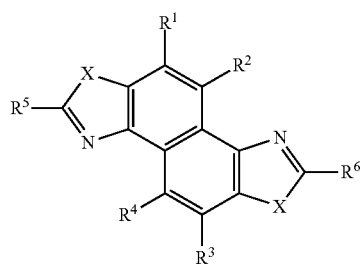

Formula (1-1)

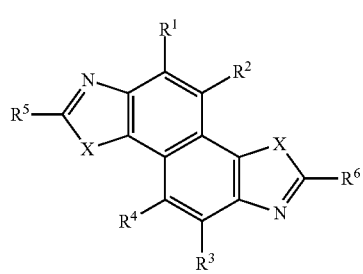

Formula (1-2)

wherein in the formulae (1-1) and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R   Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

(L-1)

(L-2)

(L-3)

(L-4)

(L-5)

(L-6)

(L-7)

(L-8)

(L-9)

-continued

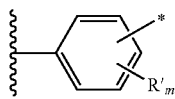
(L-10)

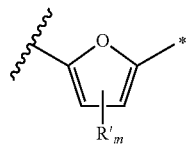
(L-11)

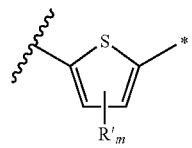
(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

(2) In the organic thin film transistor according to the item (1), at least one of $R^5$ and $R^6$ preferably represents a substituent represented by the formula (W).

(3) In the organic thin film transistor according to the item (1), the compound represented by the formula (1-1) or (1-2) is preferably a compound represented by the following formula (2-1) or (2-2):

Formula (2-1)

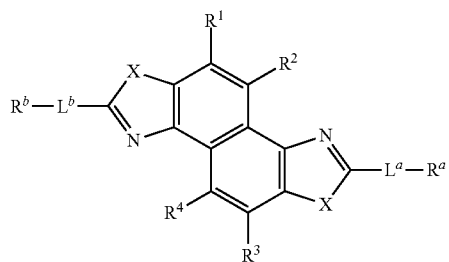

wherein in the formula (2-1), $R^1$ to $R^4$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^a$ and $R^b$ each have a number of carbon atoms in the main chain thereof of 3 or more in the case where $L^a$ and $L^b$ respectively represent a divalent linking group represented by the formula (L-1), 2 or more in the case where $L^a$ and $L^b$ respectively represent a divalent linking group represented by the formula (L-2) or (L-3), or 4 or more in the case where $L^a$ and $L^b$ respectively represent a divalent linking group represented by any one of the formulae (L-4) to (L-12), and $R^a$ and $R^b$ each represent a substituted or unsubstituted trialkylsilyl group only in the case where $L^a$ and $L^b$ adjacent to $R^a$ and $R^b$ respectively represent a divalent linking group represented by the formula (L-3), Formula (2-2)

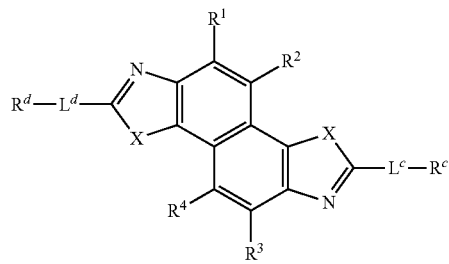

wherein in the formula (2-2), $R^1$ to $R^4$ independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^c$ and $R^d$ each have a number of carbon atoms in the main chain thereof of 3 or more in the case where $L^c$ and $L^d$ respectively represent a divalent linking group represented by the formula (L-1), 2 or more in the case where $L^c$ and $L^d$ respectively represent a divalent linking group represented by the formula (L-2) or (L-3), or 4 or more in the case where $L^c$ and $L^d$ respectively represent a divalent linking group represented by any one of the formulae (L-4) to (L-12), and $R^c$ and $R^d$ each represent a substituted or unsubstituted trialkylsilyl group only in the case where $L^c$ and $L^d$ adjacent to $R^c$ and $R^d$ respectively represent a divalent linking group represented by the formula (L-3):

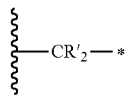
(L-1)

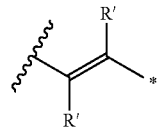
(L-2)

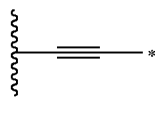
(L-3)

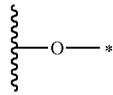
(L-4)

7

-continued (L-5)

$\xi\text{-S}\text{---}*$ (L-6)

(L-7)

(L-8)

(L-9)

(L-10)

$R'_m$ (L-11)

$R'_m$ (L-12)

$R'_m$ wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

(4) In the organic thin film transistor according to anyone of the items (1) to (3), in the formula (W), R preferably represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 4 or more in the case where L represents a divalent linking group represented by any one of the formulae (L-1) and (L-4) to (L-12), or 2 or more in the case where L represents a divalent linking group represented by the formula (L-2) or (L-3), and R represents a substituted or unsubstituted trialkylsilyl group only in the case where L adjacent to R represents a divalent linking group represented by the formula (L-3).

(5) In the organic thin film transistor according to (3) or (4), in the formula (2-1) or (2-2), $R^1$ to $R^4$ each indepen-

8 dently preferably represent a hydrogen atom, a fluorine atom, a substituted or unsubstituted alkyl group having from 1 to 12 carbon atoms, a substituted or unsubstituted alkynyl group having from 2 to 12 carbon atoms, a substituted or unsubstituted alkenyl group having from 2 to 12 carbon atoms, a substituted or unsubstituted aryl group having from 6 to 12 carbon atoms, a substituted or unsubstituted alkoxy group having from 1 to 12 carbon atoms, or a substituted or unsubstituted alkylthio group having from 1 to 12 carbon atoms.

(6) In the organic thin film transistor according to any one of the items (3) to (5), in the formula (2-1) or (2-2), all of $L^a$, $L^b$, $L^c$ and $L^d$ each preferably represent a divalent linking group represented by any one of the formulae (L-1) to (L-3), (L-10), (L-11) and (L-12), or a divalent linking group containing 2 or more of the divalent linking groups bonded to each other.

(7) In the organic thin film transistor according to any one of the items (3) to (6), in the formula (2-1) or (2-2), all of $L^a$, $L^b$, $L^c$ and $L^d$ each preferably represent a divalent linking group represented by the formula (L-1) or (L-10).

(8) In the organic thin film transistor according to any one of the items (3) to (7), in the formula (2-1) or (2-2), all $R^a$, $R^b$, $R^c$ and $R^d$ each preferably represent a substituted or unsubstituted alkyl group.

(9) In the organic thin film transistor according to any one of the items (3) to (8), in the formula (2-1) or (2-2), all $R^a$, $R^b$, $R^c$ and $R^d$ each preferably represent a linear alkyl group.

(10) A compound represented by the following formula (1-1') or (1-2'):

Formula (1-1')

Formula (1-2')

wherein in the formulae (1-1') and (1-2'), X represents a S atom or an O atom; and $R^1$ to $R^6$ each independently represent a hydrogen atom or a substituent, provided that at least one of $R^1$ to $R^6$ represents a substituent represented by the following formula (W'):

-L-R                   Formula (W')

wherein in the formula (W'), L represents a divalent linking group represented by any one of the following formulae (L-1) to (L-12), or a divalent linking group containing 2 or more divalent linking groups each represented by any one of the following formulae (L-1) to (L-12) bonded to each other;

and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 4 or more in the case where L represents a divalent linking group represented by any one of the formulae (L-1) and (L-4) to (L-12), or 2 or more in the case where L represents a divalent linking group represented by the formula (L-2) or (L-3), and R represents a substituted or unsubstituted trialkylsilyl group only in the case where L adjacent to R represents a divalent linking group represented by the formula (L-3):

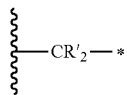
(L-1)

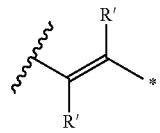
(L-2)

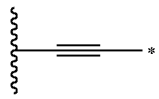
(L-3)

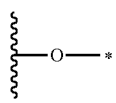
(L-4)

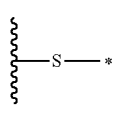
(L-5)

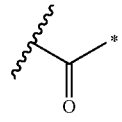
(L-6)

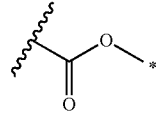
(L-7)

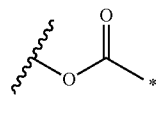
(L-8)

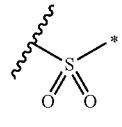
(L-9)

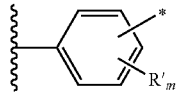
(L-10)

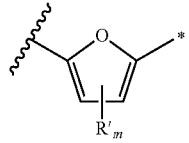
(L-11)

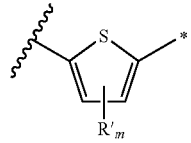
(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

(11) In the compound according to the item (10), at least one of $R^5$ and $R^6$ preferably represents a substituent represented by the formula (W).

(12) In the compound according to the item (10), the compound represented by the formula (1-1') or (1-2') is preferably a compound represented by the following formula (2-1') or (2-2'):

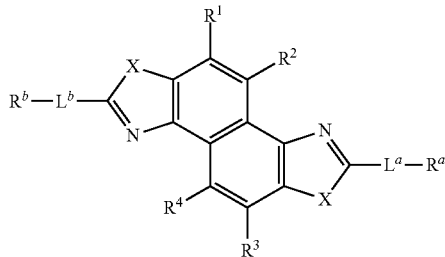

Formula (2-1')

wherein in the formula (2-1'), $R^1$ to $R^4$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^a$ and $R^b$ each have a number of carbon atoms in the main chain thereof of 4 or more in the case where $L^a$ and $L^b$ respectively represent a divalent linking group represented by any one of the formulae (L-1) and (L-4) to (L-12), or 2 or more in the case where $L^a$ and $L^b$ respectively represent a divalent linking group represented by the formula (L-2) or (L-3), and $R^a$ and $R^b$ each represent a substituted or unsubstituted trialkylsilyl group only in the case where $L^a$ and $L^b$ adjacent to $R^a$ and $R^b$ respectively represent a divalent linking group represented by the formula (L-3), Formula (2-2′)

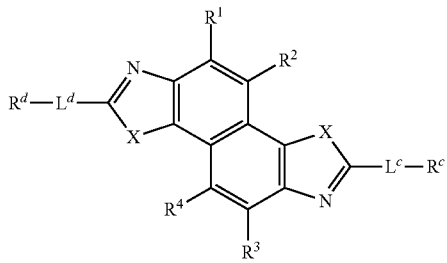

wherein in the formula (2-2′), $R^1$ to $R^4$ independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^c$ and $R^d$ each have a number of carbon atoms in the main chain thereof of 4 or more in the case where $L^c$ and $L^d$ respectively represent a divalent linking group represented by any one of the formulae (L-1) and (L-4) to (L-12), or 2 or more in the case where $L^c$ and $L^d$ respectively represent a divalent linking group represented by the formula (L-2) or (L-3), and $R^c$ and $R^d$ each represent a substituted or unsubstituted trialkylsilyl group only in the case where $L^c$ and $L^d$ adjacent to $R^c$ and $R^d$ respectively represent a divalent linking group represented by the formula (L-3):

(L-1)
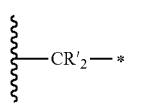

(L-2)
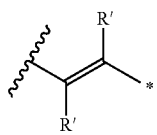

(L-3)
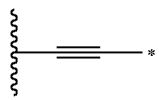

(L-4)
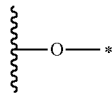

(L-5)
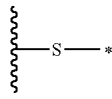

(L-6)
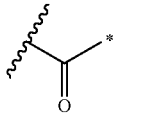

(L-7)
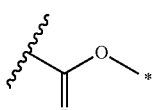

(L-8)
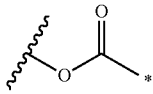

(L-9)
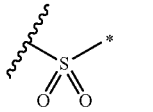

(L-10)
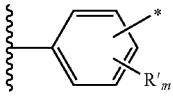

(L-11)
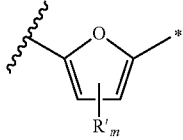

(L-12)
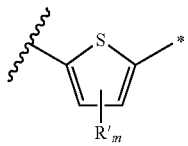

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R′ each independently represent a hydrogen atom or a substituent.

(13) In the compound according to the item (12), in the formula (2-1′) or (2-2′), $R^1$ to $R^4$ each independently preferably represent a hydrogen atom, a fluorine atom, a substituted or unsubstituted alkyl group having from 1 to 12 carbon atoms, a substituted or unsubstituted alkynyl group having from 2 to 12 carbon atoms, a substituted or unsubstituted alkenyl group having from 2 to 12 carbon atoms, a substituted or unsubstituted aryl group having from 6 to 12 carbon atoms, a substituted or unsubstituted alkoxy group having from 1 to 12 carbon atoms, or a substituted or unsubstituted alkylthio group having from 1 to 12 carbon atoms.

(14) In the compound according to the item (12) or (13), in the formula (2-1′) or (2-2′), all of $L^a$, $L^b$, $L^c$ and $L^d$ each preferably represent a divalent linking group represented by any one of the formulae (L-1) to (L-3), (L-10), (L-11) and (L-12), or a divalent linking group containing 2 or more of the divalent linking groups bonded to each other.

(15) In the compound according to any one of the items (12) to (14), in the formula (2-1′) or (2-2′), all of $L^a$, $L^b$, $L^c$ and $L^d$ each preferably represent a divalent linking group represented by the formula (L-1) or (L-10).

(16) In the compound according to any one of the items (12) to (15), in the formula (2-1') or (2-2'), all $R^a$, $R^b$, $R^c$ and $R^d$ each preferably represent a substituted or unsubstituted alkyl group.

(17) In the compound according to any one of the items (12) to (16), in the formula (2-1') or (2-2'), all $R^a$, $R^b$, $R^c$ and $R^d$ each preferably represent a linear alkyl group.

(18) An organic semiconductor material for a non-light emitting organic semiconductor device, containing the compound represented by the formula (1-1) or (1-2) according to the item (1).

(19) A material for an organic thin film transistor, containing the compound represented by the formula (1-1) or (1-2) according to the item (1).

(20) A coating solution for a non-light emitting organic semiconductor device, containing the compound represented by the formula (1-1) or (1-2) according to the item (1).

(21) A coating solution for a non-light emitting organic semiconductor device, containing the compound represented by the formula (1-1) or (1-2) according to the item (1), and a polymer binder.

(22) An organic semiconductor thin film for a non-light emitting organic semiconductor device, containing the compound represented by the formula (1-1) or (1-2) according to the item (1).

(23) An organic semiconductor thin film for a non-light emitting organic semiconductor device, containing the compound represented by the formula (1-1) or (1-2) according to the item (1), and a polymer binder.

(24) The organic semiconductor thin film for a non-light emitting organic semiconductor device according to the item (22) or (23) is preferably produced by a solution coating method.

According to the invention, an organic thin film transistor may be provided that has a high carrier mobility and a small change in the threshold voltage after repeated driving.

BRIEF DESCRIPTION OF DRAWINGS

In FIGS. 1 and 2, 11 is substrate, 12 is electrode, 13 is insulating layer, 14 is semiconductor active layer (organic material layer or organic semiconductor layer), 15a, 15b are each electrode, 31 is substrate, 32 is electrode, 33 is insulating layer, 34a, 34b are each electrode, and 35 is semiconductor active layer (organic material layer or organic semiconductor layer).

DESCRIPTION OF EMBODIMENTS

Figure 1:
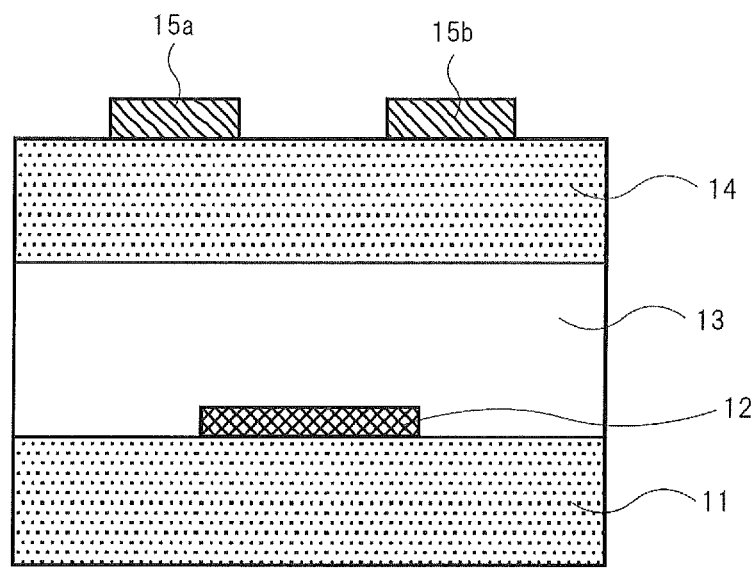
FIG. 1 is a schematic illustration showing a cross sectional structure of one example of the organic thin film transistor of the invention.

The invention will be described in detail below. The description for the constitutional components shown below may be made with reference to representative embodiments and specific examples, but the invention is not limited to the embodiments and the examples. In the description, a numerical range expressed with reference to an upper limit and/or a lower limit means a range that includes the upper limit and/or the lower limit.

In the invention, the hydrogen atom that is referred without any particular discrimination in the description of the formulae herein includes isotopes thereof (such as a deuterium atom). The atoms constituting the substituents also include isotopes thereof.

Organic Thin Film Transistor

The organic thin film transistor of the invention contains a compound represented by the following formula (1-1) or (1-2) in a semiconductor active layer:

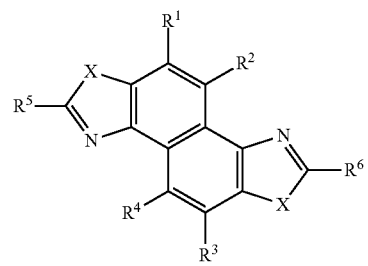

Formula (1-1)

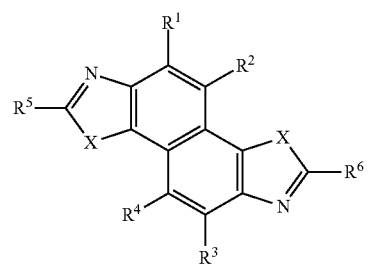

Formula (1-2)

wherein in the formulae (1-1) and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R          Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

(L-1)

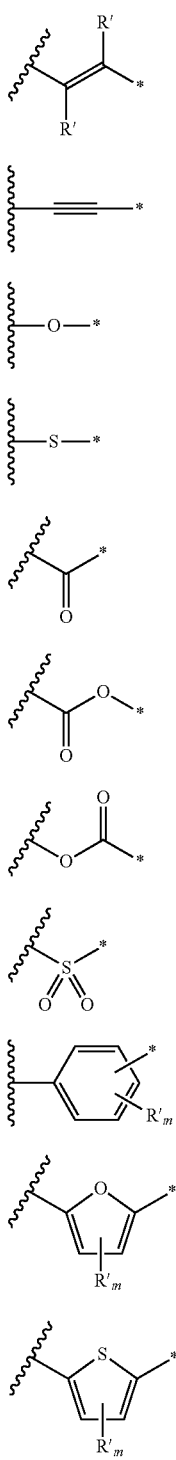

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

According to the constitution, the organic thin film transistor of the invention has a high carrier mobility and a small change in the threshold voltage after repeated driving.

The compound represented by the formula (1-1) or (1-2) has a substituent represented by the formula (W) as at least one of $R^1$ to $R^6$, and thus is preferred from the standpoint of the applicability of the material to a solution process and the molecular orientation in the film, and a semiconductor material capable of forming an organic thin film advantageous for carrier transport may be provided thereby. Accordingly, an organic thin film transistor having a high carrier mobility may be obtained. Furthermore, the compound may enhance the production efficiency of the organic thin film capable of being applied to an organic thin film transistor, may suppress the production cost thereof, and may enhance the chemical and physical stability of the thin film.

For reducing the change in the threshold voltage after repeated driving, there are such requirements as chemical stability of the organic semiconductor material (particularly, air oxidation resistance and redox stability), thermal stability in the form of a thin film, a large film density capable of preventing air and water from invading, a film quality with less defects capable of preventing charges from being accumulated, and the like. It is considered that the compound represented by the formula (1-1) or (1-2) satisfies these requirements and thus has a small change in the threshold voltage after repeated driving. Accordingly, the organic thin film transistor of the invention having a less change in the threshold voltage after repeated driving has a semiconductor active layer that has a high chemical stability, a high film density, and the like, and thus effectively functions as a transistor for a prolonged period of time.

JP-A-05-214335, JP-B-48-041118, Ukrains' kii Khemichnii Zhurnal, 22, 772 (1956), Journal of the Chemical Society [Section] C: Organic, (21), 2212-20 (1967), and Journal fuer Praktische Chemie (Leipzig), 18, 292-6 (1962) do not describe or suggest the use of the compounds described in the literature in an organic thin film transistor, and the high carrier mobility and the small change in the threshold voltage after repeated driving of the organic thin film transistor of the invention using the compound represented by the formula (1-1) or (1-2) are superior effects that are not expected from the characteristics of the compounds described in the literatures.

Preferred embodiments of the compound of the invention, the organic thin film transistor of the invention, and the like will be described below.

Compound Represented by Formula (1-1) or (1-2) and Compound Represented by Formula (1-1') or (1-2')

The compound represented by the formula (1-1) or (1-2) contained in the semiconductor active layer of the organic thin film transistor of the invention will be described.

The compound of the invention is represented by the formula (1-1') or (1-2'):

Formula (1-1')

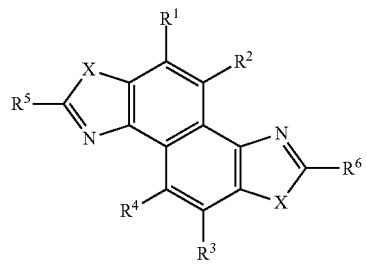

Formula (1-2')

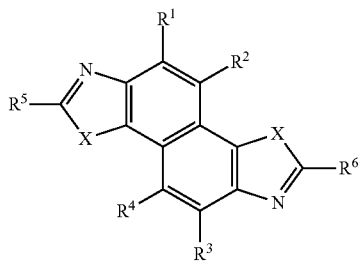

wherein in the formulae (1-1') and (1-2'), X represents a S atom or an O atom; and $R^1$ to $R^6$ each independently represent a hydrogen atom or a substituent, provided that at least one of $R^1$ to $R^6$ represents a substituent represented by the following formula (W'):

-L-R    Formula (W')

wherein in the formula (W'), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 4 or more in the case where L represents a divalent linking group represented by any one of the formulae (L-1) and (L-4) to (L-12), or 2 or more in the case where L represents a divalent linking group represented by the formula (L-2) or (L-3), and R represents a substituted or unsubstituted trialkylsilyl group only in the case where L adjacent to R represents a divalent linking group represented by the formula (L-3):

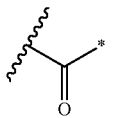 (L-1)

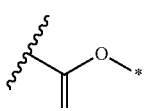 (L-2)

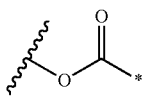 (L-3)

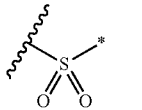 (L-4)

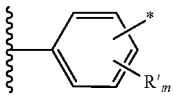 (L-5)

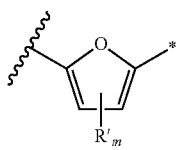 (L-6)

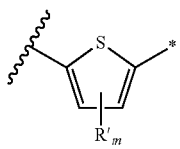 (L-7)

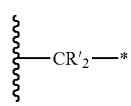 (L-8)

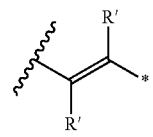 (L-9)

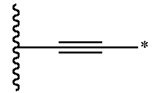 (L-10)

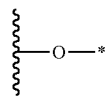 (L-11)

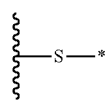 (L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

The compound represented by the formula (1-1') or (1-2') of the invention is contained in the semiconductor active layer described later of the organic thin film transistor of the invention. Accordingly, the compound of the invention may be used as a material for an organic thin film transistor.

The formulae (1-1') and (1-2') correspond to the formulae (1-1) and (1-2), respectively, that are in the case where in the formula (W), R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 4 or more in the case where L represents a divalent linking group represented by any one of the formulae (L-1) and (L-4) to (L-12), or 2 or more in the case where L represents a divalent linking group represented by the formula (L-2) or (L-3), and R represents a substituted or unsubstituted trialkylsilyl group only in the case where L adjacent to R represents a divalent linking group represented by the formula (L-3). The compound represented by the formula (1-1') or (1-2') is a novel compound in the group of compounds represented by the formula (1-1) or (1-2).

The preferred ranges for the formulae (1-1') and (1-2') are the same as the preferred ranges for the formulae (1-1) and (1-2) described later.

The preferred ranges of the compound represented by the formula (1-1) or (1-2) will be described.

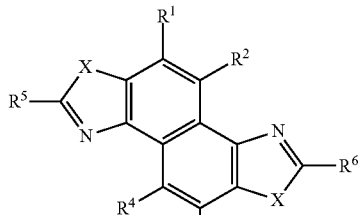

Formula (1-1)

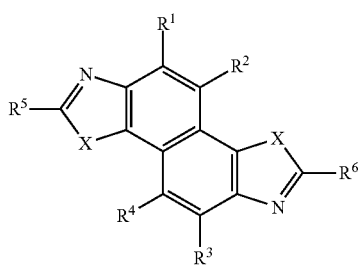

Formula (1-2)

wherein in the formulae (1-1) and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R                Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

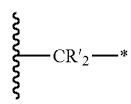

(L-1)

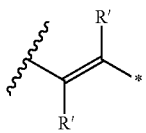

(L-2)

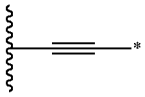

(L-3)

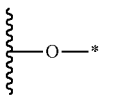

(L-4)

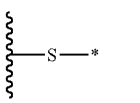

(L-5)

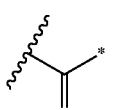

(L-6)

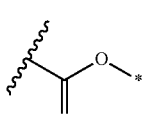

(L-7)

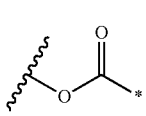

(L-8)

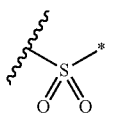

(L-9)

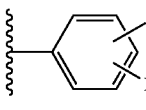

(L-10)

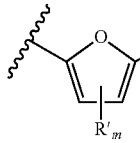

(L-11)

(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

In the formula (1-1) or (1-2), $R^1$ to $R^6$ each independently represent a hydrogen atom or a substituent, provided that at least one of $R^1$ to $R^6$ represents a substituent represented by the following formula (W).

The compound represented by the formula (1-1) or (1-2) may contain a substituent other than the substituent represented by the formula (W).

Examples of the substituent that may be $R^1$ to $R^6$ in the formula (1-1) or (1-2) include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group ($-B(OH)_2$), a phosphato group ($-PO(OH)_2$), a sulphato group ($-OSO_3H$), and other known groups.

Among these, a halogen atom, an alkyl group and an aryl group are preferred, and a fluorine atom, an alkyl group having from 1 to 3 carbon atoms and a phenyl group are more preferred.

In the compound represented by the formula (1-1) or (1-2), the number of the substituent other than the substituent represented by the formula (W) in $R^1$ to $R^6$ is preferably from 0 to 4, more preferably from 0 to 2, and particularly preferably 0.

The substituent represented by the formula (W) will be described. In the description for the formulae (L-1) to (L-12), the main chain means the longest portion in the continuous C—C bonds constituting the alkyl group, and the number of carbon atoms in the main chain means the number of carbon atoms constituting the main chain. For example, a n-hexyl group has a number of carbon atoms in the main chain of 6, an isobutyl group has a number of carbon atoms in the main chain of 3, a t-butyl group has a number of carbon atoms in the main chain of 2, and a 2-ethylhexyl group has a number of carbon atoms in the main chain of 6.

In the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

(L-1)

(L-2)

(L-3)

(L-4)

(L-5)

(L-6)

(L-7)

(L-8)

(L-9)

(L-10)

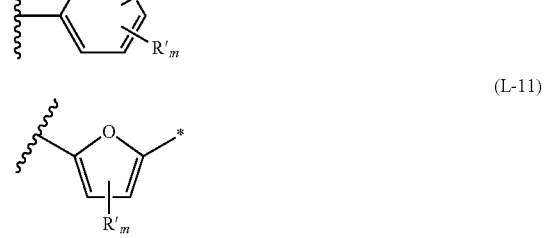
(L-11)

-continued

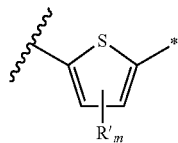
(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

In the formulae (L-1) to (L-12), * represents a position bonded to R in the formula (W).

In the case where L represents a divalent linking group containing divalent linking groups each represented by any one of the formulae (L-1) to (L-12) bonded to each other, the number of the divalent linking groups each represented by any one of the formulae (L-1) to (L-12) bonded to each other is preferably from 2 to 4, and more preferably 2 or 3.

In the formulae (L-1) to (L-12), it is also preferred that any one of the formulae (L-1) to (L-12) is further inserted between * and R to form L that represents a linking group containing divalent linking groups each represented by any one of the formulae (L-1) to (L-12) bonded to each other.

Examples of the substituent R' in the formulae (L-1), (L-2), (L-10), (L-11) and (L-12) include the groups that are shown as examples of the other substituent that may be $R^1$ to $R^6$ in the formula (1-1) and (1-2).

In the formula (L-10), m represents 4; and in the formulae (L-11) and (L-12), m represents 2.

L preferably represents a divalent linking group represented by any one of the formulae (L-1) to (L-6), (L-10), (L-11) and (L-12) or a divalent linking group containing 2 or more of the divalent linking groups bonded to each other, more preferably a divalent linking group represented by any one of the formulae (L-1) to (L-3), (L-10), (L-11) and (L-12) or a divalent linking group containing 2 or more of the divalent linking groups bonded to each other from the standpoint of the chemical stability and the carrier transport property, particularly preferably a divalent linking group represented by the formula (L-1) or (L-10) or a divalent linking group containing 2 or more of the divalent linking groups bonded to each other, further particularly preferably a divalent linking group represented by the formula (L-1) or (L-10), and still further particularly preferably a divalent linking group represented by the formula (L-1).

In the formula (W), R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3).

In the case where R in the formula (W) represents a substituted or unsubstituted alkyl group, the number of carbon atoms in the main chain of the alkyl group in the case where L represents a divalent linking group represented by the formula (L-1) is 3 or more, preferably from 3 to 12, and more preferably from 3 to 10 from the standpoint of the enhancement of the carrier mobility.

In the case where R in the formula (W) represents a substituted or unsubstituted alkyl group, the number of carbon atoms in the main chain of the alkyl group in the case where L represents a divalent linking group represented by the formula (L-2) or (L-3) is 2 or more, preferably from 2 to 12, more preferably from 3 to 10 from the standpoint of the enhancement of the carrier mobility, and particularly preferably from 4 to 9 from the standpoint of the further enhancement of the carrier mobility.

In the case where R in the formula (W) represents a substituted or unsubstituted alkyl group, the number of carbon atoms in the main chain of the alkyl group in the case where L represents a divalent linking group represented by any one of the formulae (L-4) to (L-9) is 4 or more, preferably 5 or more from the standpoint of the enhancement of the carrier mobility, and particularly preferably from 6 to 12 from the standpoint of the further enhancement of the carrier mobility.

In the case where R in the formula (W) represents a substituted or unsubstituted alkyl group, the number of carbon atoms in the main chain of the alkyl group in the case where L represents a divalent linking group represented by any one of the formulae (L-10) to (L-12) is 4 or more, preferably from 4 to 12, and more preferably from 6 to 12 from the standpoint of the enhancement of the carrier mobility.

In the case where L represents a divalent linking group containing 2 or more divalent linking groups each represented by any one of the formulae (L-1) to (L-12) bonded to each other, the preferred range of the number of carbon atoms in the main chain of the substituted or unsubstituted alkyl group is determined by the kind of the formulae (L-1) to (L-12) that is adjacent to R.

In the compound represented by the formula (1-1) or (1-2), in the case where the group represented by the formula (W) contains an alkyl group, a high carrier mobility may be obtained when the total number of carbon atoms in the main chains of the alkyl groups of L and R is 4 or more.

The alkyl group that may be R may be any one of linear, branched and cyclic, and is particularly preferably a linear alkyl group from the standpoint of the enhancement of the carrier mobility. In the case where R represents an alkyl group having a substituent, examples of the substituent include a halogen atom, and a fluorine atom is preferred. In the case where R represents an alkyl group having a fluorine atom, the alkyl group may be a perfluoroalkyl group, in which all the hydrogen atoms of the alkyl group are replaced by fluorine atoms.

In the case where R in the formula (W) represents an oligooxyethylene group having a repeating number v of an oxyethylene group of 2 or more, the oxyethylene group represented by R herein means a group represented by —$(CH_2CH_2)_vOY$ (wherein the repeating number v of an oxyethylene unit is an integer of 2 or more, and Y as the terminal group represents a hydrogen atom or a substituent). In the case where Y as the terminal group of the oligooxyethylene group is a hydrogen atom, the group is a hydroxyl group. The repeating number v of an oxyethylene unit is preferably from 2 to 4, and more preferably from 2 to 3. The terminal hydroxyl group of the oligooxyethylene group is preferably blocked, i.e., Y preferably represents a substituent. In this case, the hydroxyl group is preferably blocked with an alkyl group having from 1 to 3 carbon atoms, i.e., Y preferably represents an alkyl group having from 1 to 3 carbon atoms, and Y more preferably represents a methyl group or an ethyl group, and particularly preferably a methyl group.

In the case where R in the formula (W) represents an oligosiloxane group having 2 or more silicon atoms, the repeating number of a siloxane unit is preferably from 2 to 4, and more preferably from 2 to 3. The Si atom is preferably bonded to a hydrogen atom or an alkyl group. In the case where the Si atom is bonded to an alkyl group, the number of carbon atoms of the alkyl group is preferably from 1 to 3, and for example, a methyl group or an ethyl group is preferably bonded thereto. The Si atom may be bonded to the same alkyl groups or may be bonded to different alkyl groups or a hydrogen atom. The siloxane units constituting the oligosiloxane group may be all the same as each other or different from each other, and are preferably all the same as each other.

In the formula (W), only in the case where L adjacent to R represents a divalent linking group represented by the formula (L-3), R may represent a substituted or unsubstituted trialkylsilyl group. In the case where R in the formula (W) represents a substituted or unsubstituted trialkylsilyl group, the alkyl group bonded to the Si atom preferably has from 1 to 3 carbon atoms, and for example, a methyl group, an ethyl group, an isopropyl group or the like is preferably bonded to the Si atom. The alkyl groups bonded to the Si atom may be the same as or different from each other. In the case where R represents a trialkylsilyl group having a substituent, the substituent is not particularly limited.

In the compound represented by the formula (1-1) or (1-2), the number of the substituent that is represented by the formula (W) in $R^1$ to $R^6$ is preferably from 1 to 4, more preferably from 1 to 2, and particularly preferably 2.

In the formula (1-1) or (1-2) in the invention, at least one of $R^5$ and $R^6$ preferably represents a substituent represented by the formula (W) from the standpoint of the achievement of both the solubility and the carrier mobility. Furthermore, both $R^5$ and $R^6$ are more preferably substituted by a substituent represented by the formula (W) from the standpoint of the achievement of both the solubility and the carrier mobility.

It is considered that the reason why these positions are preferred as the substitution positions in the formula (1-1) or (1-2) is that the compound is excellent in chemical stability and is preferred from the standpoint of the HOMO level and the molecular packing in the film. In particular, in the formula (1-1) or (1-2), when two positions of $R^5$ and $R^6$ each represent the substituent, a high carrier concentration may be obtained.

In the invention, the compound represented by the formula (1-1) or (1-2) is preferably a compound represented by the following formula (2-1) or (2-2) from the standpoint of the enhancement of the carrier mobility while enhancing the solubility.

Formula (2-1)

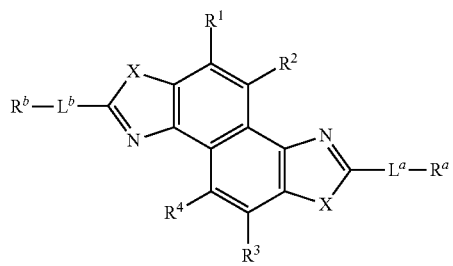

wherein in the formula (2-1), $R^1$ to $R^4$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^a$ and $R^b$ each have a number of carbon atoms in the main chain thereof of 3 or more in the case where $L^a$ and $L^b$ respectively represent a divalent linking group represented by the formula (L-1), 2 or more in the case where $L^a$ and $L^b$ respectively represent a divalent linking group represented by the formula (L-2) or (L-3), or 4 or more in the case where $L^a$ and $L^b$ respectively represent a divalent linking group represented by any one of the formulae (L-4) to (L-12), and $R^a$ and $R^b$ each represent a substituted or unsubstituted trialkylsilyl group only in the case where $L^a$ and $L^b$ adjacent to $R^a$ and $R^b$ respectively represent a divalent linking group represented by the formula (L-3), Formula (2-2)

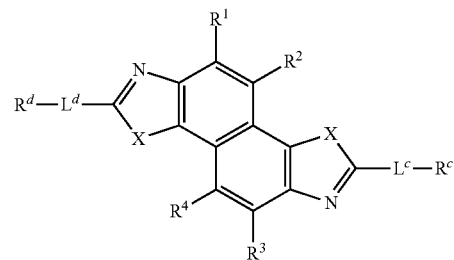

wherein in the formula (2-2), $R^1$ to $R^4$ independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^c$ and $R^d$ each have a number of carbon atoms in the main chain thereof of 3 or more in the case where $L^c$ and $L^d$ respectively represent a divalent linking group represented by the formula (L-1), 2 or more in the case where $L^c$ and $L^d$ respectively represent a divalent linking group represented by the formula (L-2) or (L-3), or 4 or more in the case where $L^c$ and $L^d$ respectively represent a divalent linking group represented by any one of the formulae (L-4) to (L-12), and $R^c$ and $R^d$ each represent a substituted or unsubstituted trialkylsilyl group only in the case where $L^c$ and $L^d$ adjacent to $R^c$ and $R^d$ respectively represent a divalent linking group represented by the formula (L-3):

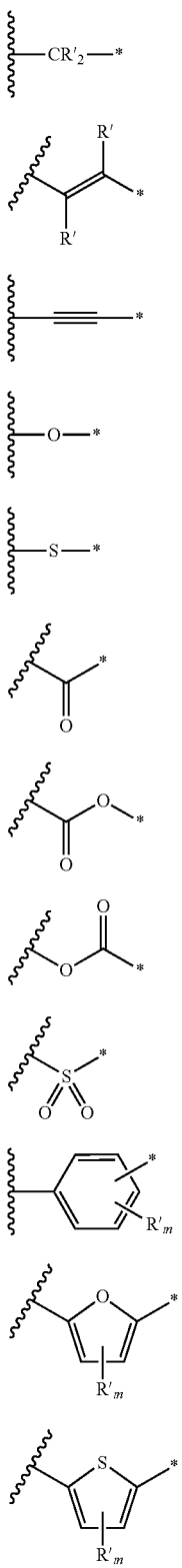

(L-1)
(L-2)
(L-3)
(L-4)
(L-5)
(L-6)
(L-7)
(L-8)
(L-9)
(L-10)
(L-11)
(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

In the formulae (2-1) and (2-2), the preferred ranges of the substituents represented by $R^1$ to $R^4$ are the same as the preferred ranges of the substituents represented by $R^1$ to $R^6$ in the formulae (1-1) and (1-2) other than the substituent represented by the formula (W).

In the formula (2-1), the preferred ranges of $L^a$ and $L^b$ are the same as the preferred ranges of L in the formula (W). $L^a$ and $L^b$ are preferably the same as each other.

In the formula (2-2), the preferred ranges of $L^c$ and $L^d$ are the same as the preferred ranges of L in the formula (W). $L^c$ and $L^d$ are preferably the same as each other.

In the formula (2-1), the preferred ranges of $R^a$ and $R^b$ are the same as the preferred ranges of R in the formula (W). $R^a$ and $R^b$ are preferably the same as each other.

In the formula (2-2), the preferred ranges of $R^c$ and $R^d$ are the same as the preferred ranges of R in the formula (W). $R^c$ and $R^d$ are preferably the same as each other.

In the formulae (2-1) and (2-2), all $R^a$, $R^b$, $R^c$ and $R^d$ each preferably represent a substituted or unsubstituted alkyl group, and more preferably a linear alkyl group. The preferred ranges of the numbers of carbon atoms in the main chains of the alkyl groups represented by $R^a$, $R^b$, $R^c$ and $R^d$ are the same as the preferred ranges of the number of carbon atoms in the main chain of the alkyl group represented by R in the formula (W).

In the formulae (2-1) and (2-2), all of $L^a$, $L^b$, $L^c$ and $L^d$ each preferably represent a divalent linking group represented by any one of the formulae (L-1) to (L-3), (L-10), (L-11) and (L-12), or a divalent linking group containing 2 or more of the divalent linking groups bonded to each other, and more preferably a divalent linking group represented by the formula (L–1) or (L-10).

In the formulae (2-1) and (2-2), $R^a$, $R^b$, $R^c$ and $R^d$ each preferably represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^a$, $R^b$, $R^c$ and $R^d$ each have a number of carbon atoms in the main chain thereof of 4 or more in the case where $L^a$, $L^b$, $L^c$ and $L^d$ respectively represent a divalent linking group represented by any one of the formulae (L-1) and (L-4) to (L-12), or 2 or more in the case where $L^a$, $L^b$, $L^c$ and $L^d$ respectively represent a divalent linking group represented by the formula (L-2) or (L-3), and $R^a$, $R^b$, $R^c$ and $R^d$ each represent a substituted or unsubstituted trialkylsilyl group only in the case where $L^a$, $L^b$, $L^c$ and $L^d$ adjacent to $R^a$, $R^b$, $R^c$ and $R^d$ respectively represent a divalent linking group represented by the formula (L-3).

Accordingly, the compound represented by the formula (2-1) or (2-2) is preferably a compound represented by the following formula (2-1') or (2-2'). The preferred ranges for the groups in the formulae (2-1') and (2-2') are the same as the preferred ranges for the groups in the formulae (2-1) and (2-2).

Formula (2-1')

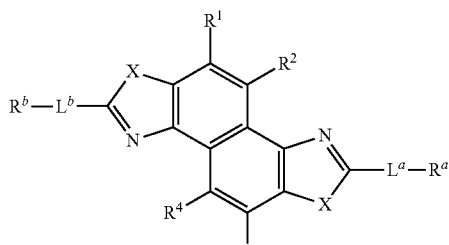

wherein in the formula (2-1'), $R^1$ to $R^4$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^a$ and $R^b$ each have a number of carbon atoms in the main chain thereof of 4 or more in the case where $L^a$ and $L^b$ respectively represent a divalent linking group represented by any one of the formulae (L-1) and (L-4) to (L-12), or 2 or more in the case where $L^a$ and $L^b$ respectively represent a divalent linking group represented by the formula (L-2) or (L-3), and $R^a$ and $R^b$ each represent a substituted or unsubstituted trialkylsilyl group only in the case where $L^a$ and $L^b$ adjacent to $R^a$ and $R^b$ respectively represent a divalent linking group represented by the formula (L-3), Formula (2-2')

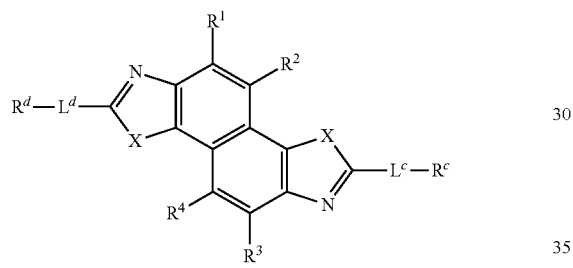

wherein in the formula (2-2'), $R^1$ to $R^4$ independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^c$ and $R^d$ each have a number of carbon atoms in the main chain thereof of 4 or more in the case where $L^c$ and $L^d$ respectively represent a divalent linking group represented by any one of the formulae (L-1) and (L-4) to (L-12), or 2 or more in the case where $L^c$ and $L^d$ respectively represent a divalent linking group represented by the formula (L-2) or (L-3), and $R^c$ and $R^d$ each represent a substituted or unsubstituted trialkylsilyl group only in the case where $L^c$ and $L^d$ adjacent to $R^c$ and $R^d$ respectively represent a divalent linking group represented by the formula (L-3):

 (L-1)

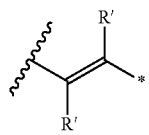 (L-2)

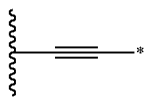 (L-3)

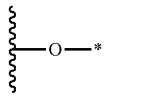 (L-4)

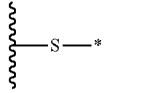 (L-5)

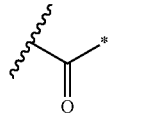 (L-6)

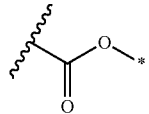 (L-7)

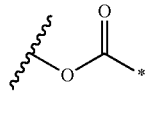 (L-8)

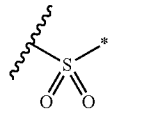 (L-9)

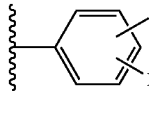 (L-10)

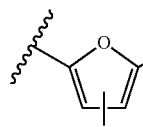 (L-11)

(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

Specific examples of the compound represented by the formula (1-1) to (1-2) are shown below, but the compound represented by the formula (1-1) to (1-2) capable of being used in the invention is not construed as being limited to the specific examples.

Compound 1

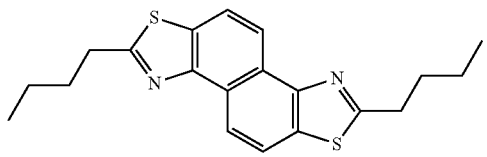

Compound 1A

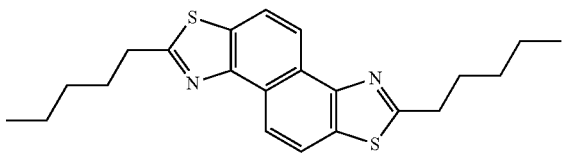

Compound 2

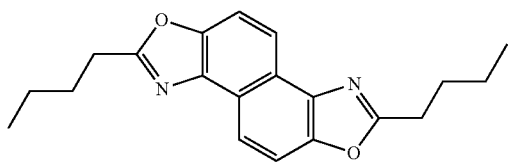

Compound 3

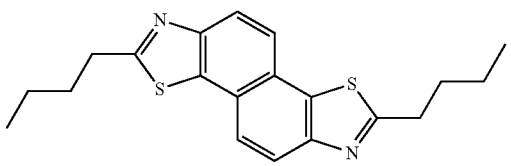

Compound 4

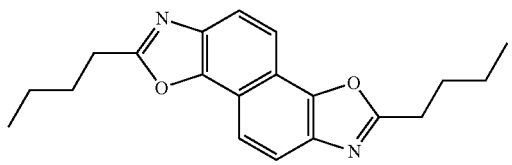

Compound 5

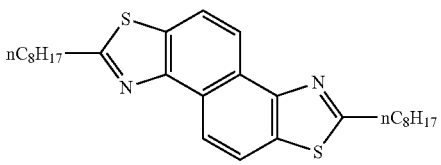

化合物 6

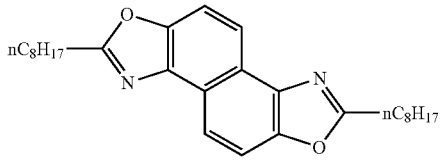

Compound 7

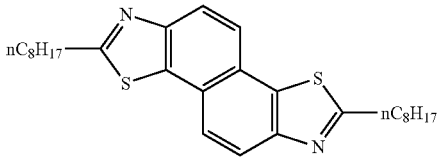

Compound 8

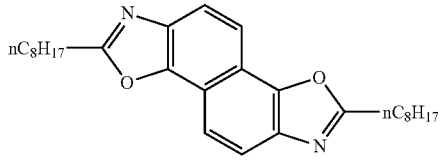

Compound 9

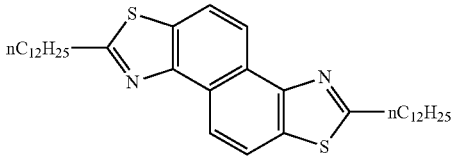

Compound 10

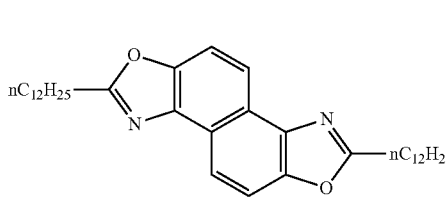

Compound 11

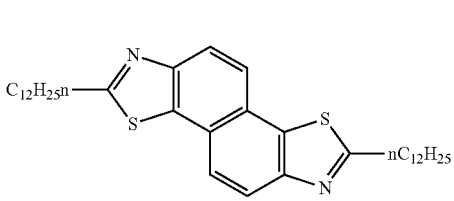

Compound 12

Compound 13

Compound 14

Compound 15

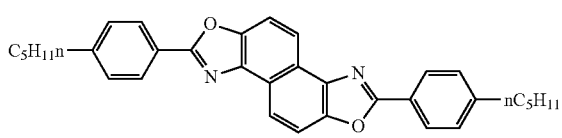

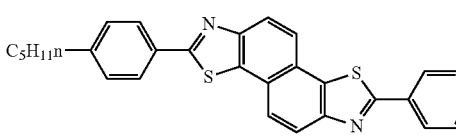

-continued
Compound 16
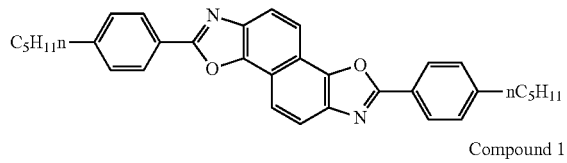
Compound 17
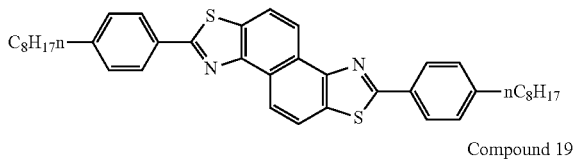
Compound 18
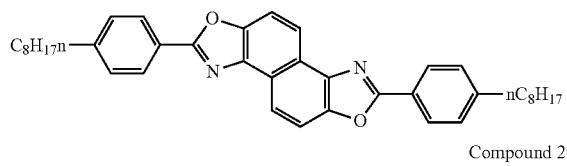
Compound 19
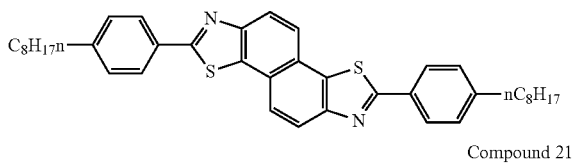
Compound 20
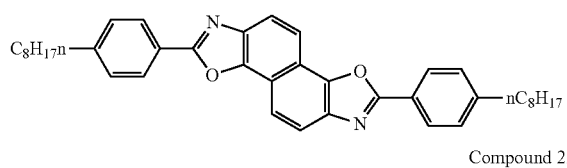
Compound 21
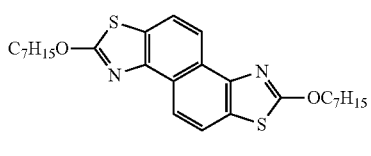
Compound 22
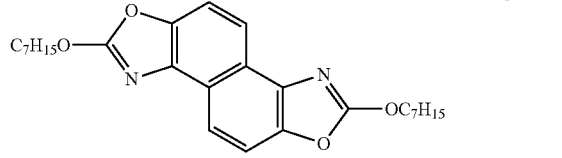
Compound 23
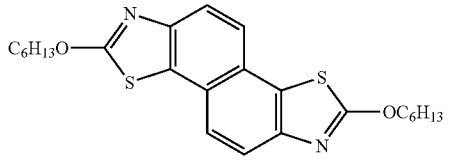
Compound 24
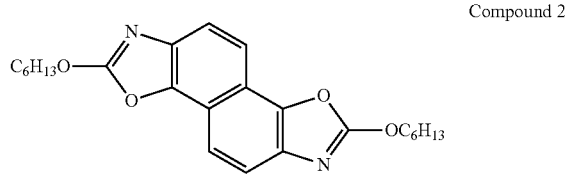
Compound 25
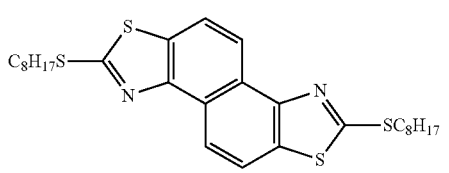
Compound 26
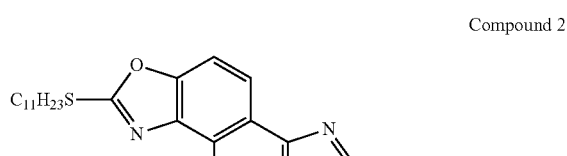
Compound 27
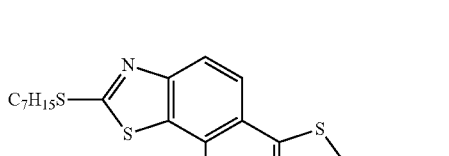
Compound 28
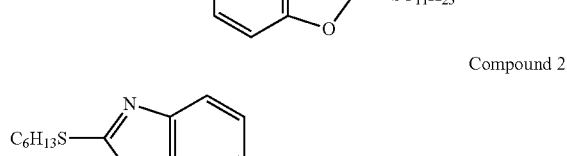
Compound 29
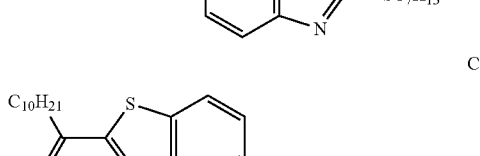
Compound 30
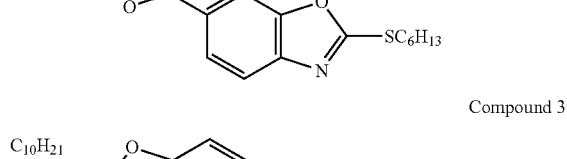
Compound 31
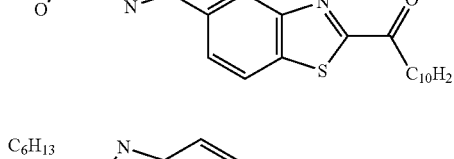
Compound 32
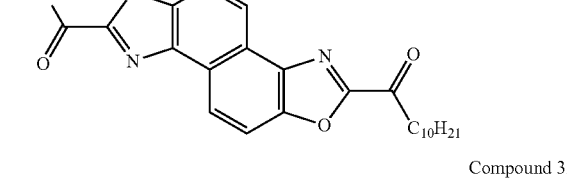
Compound 33
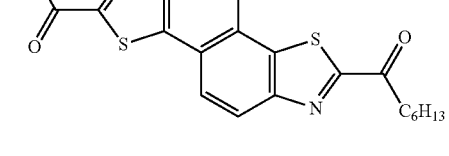
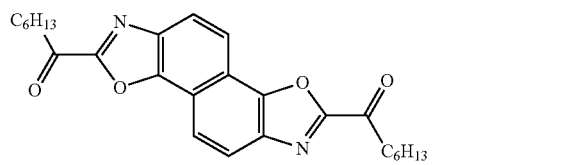
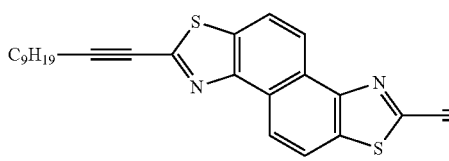

-continued
Compound 34
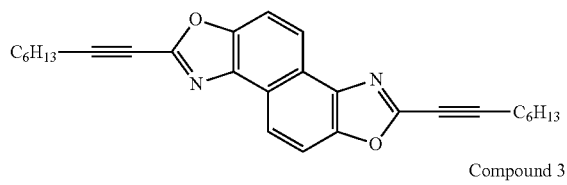
Compound 35
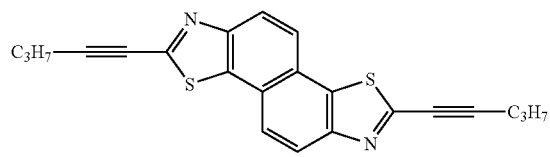
Compound 36
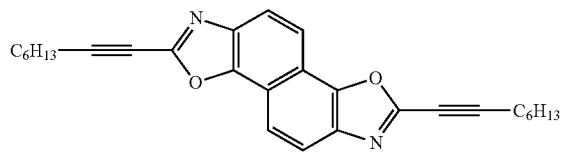
Compound 37
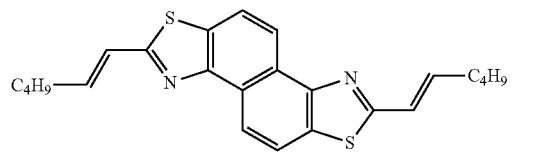
Compound 38
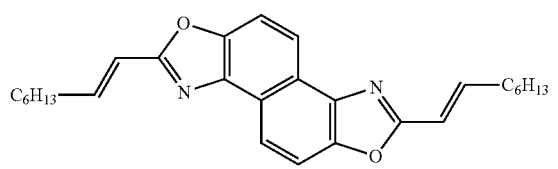
Compound 39
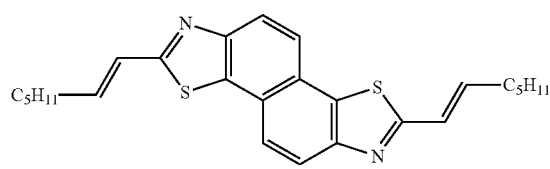
Compound 40
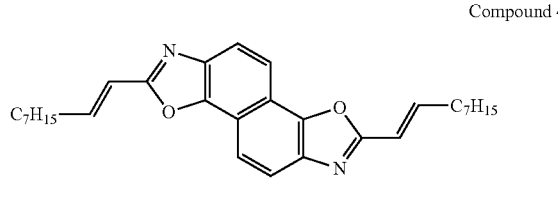
Compound 41
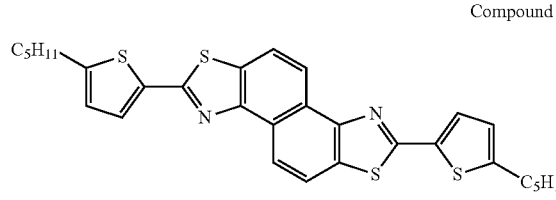
Compound 42
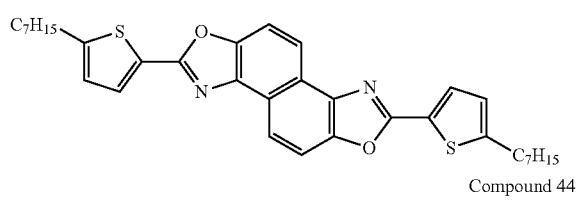
Compound 43
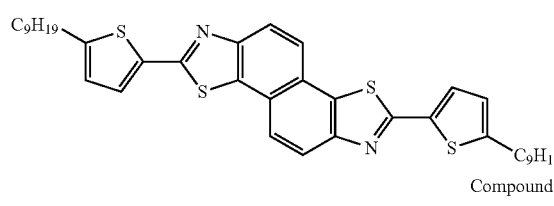
Compound 44
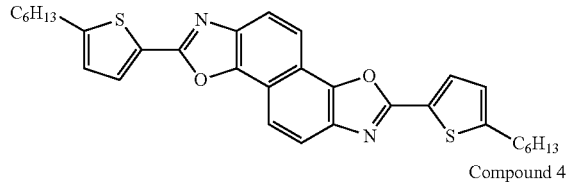
Compound 45
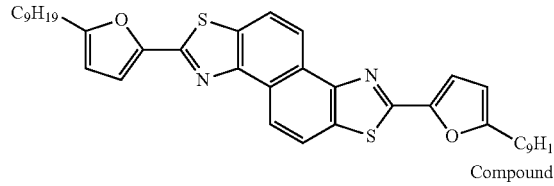
Compound 46
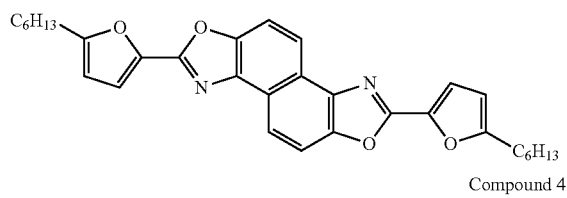
Compound 47
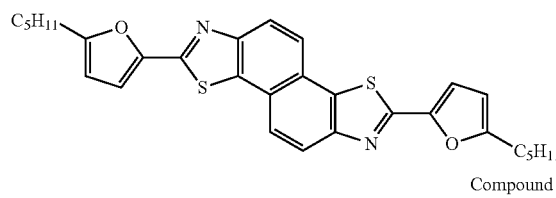
Compound 48
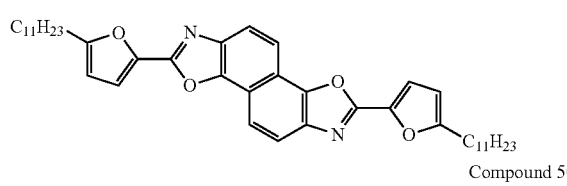
Compound 49
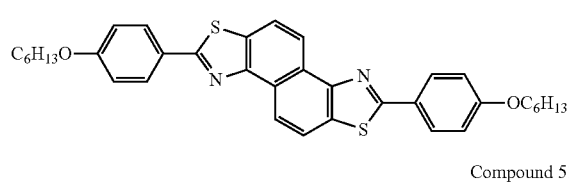
Compound 50
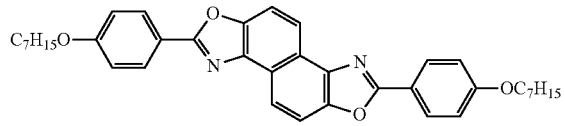
Compound 51
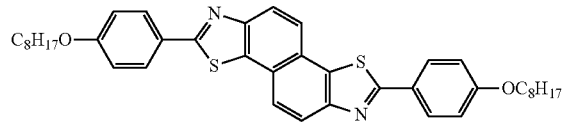

-continued
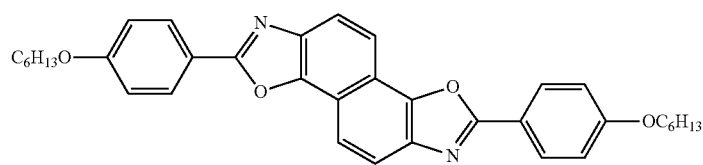
Compound 52
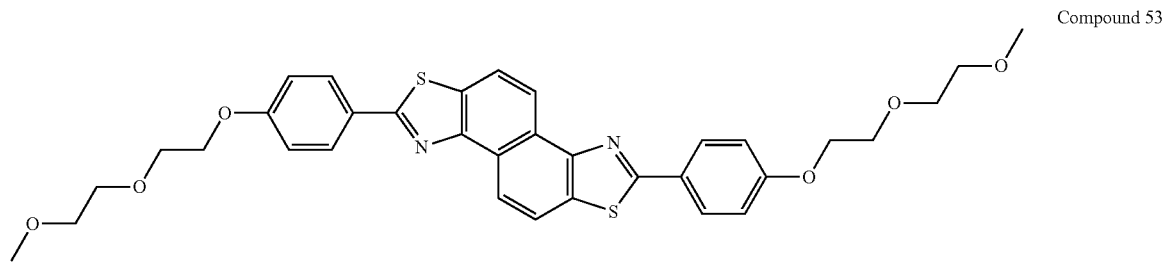
Compound 53
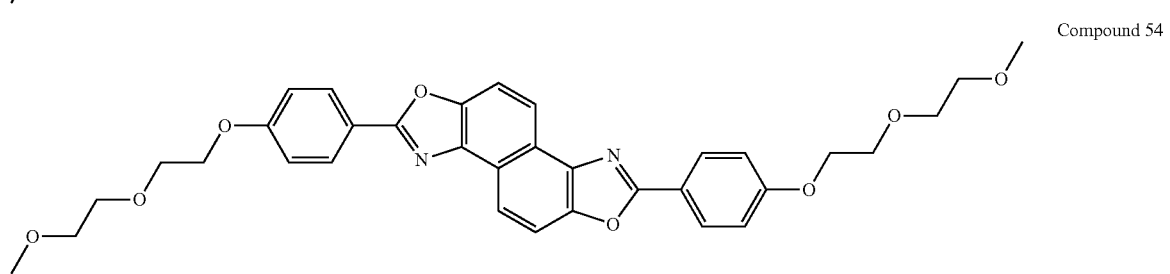
Compound 54
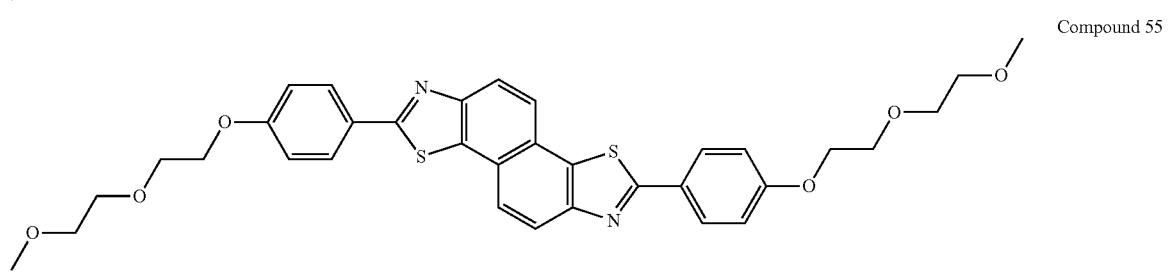
Compound 55
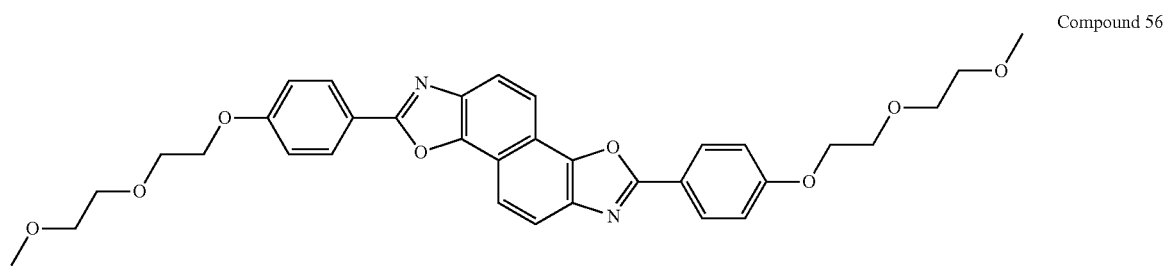
Compound 56
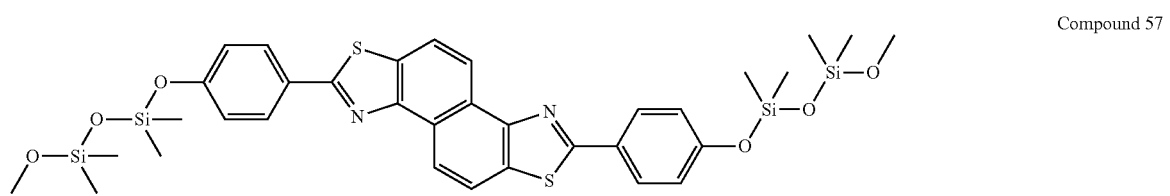
Compound 57
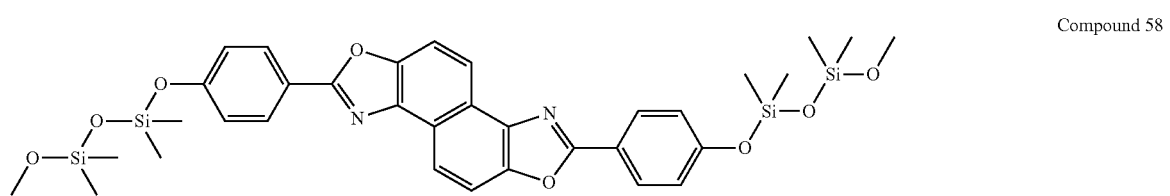
Compound 58

-continued
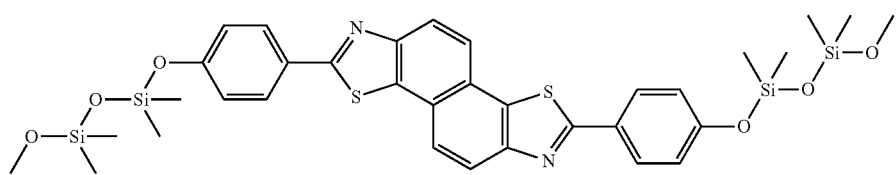
Compound 59
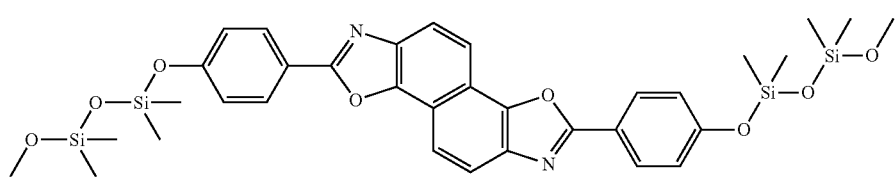
Compound 60
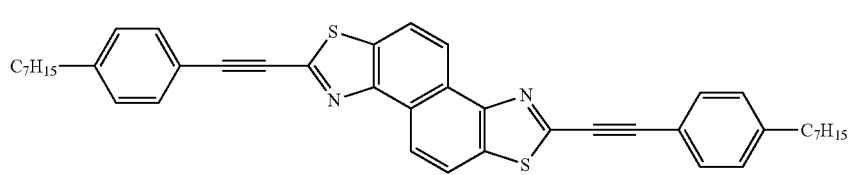
Compound 61
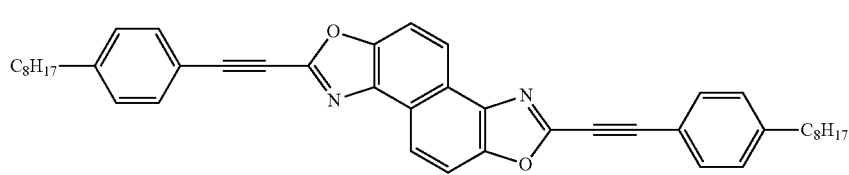
Compound 62
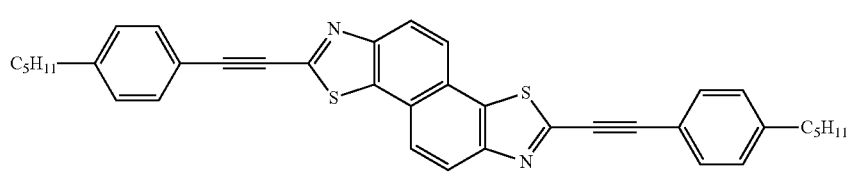
Compound 63
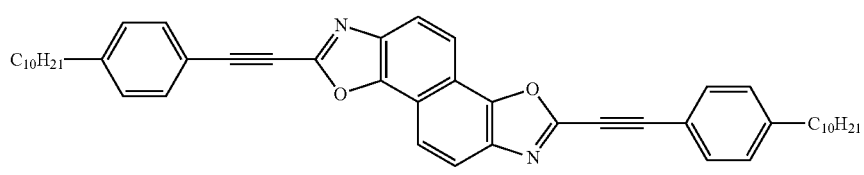
Compound 64
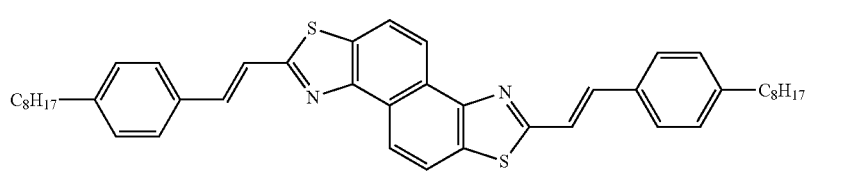
Compound 65
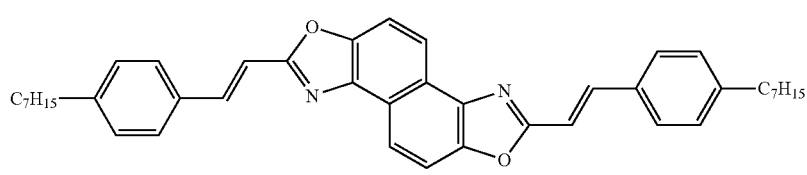
Compound 66
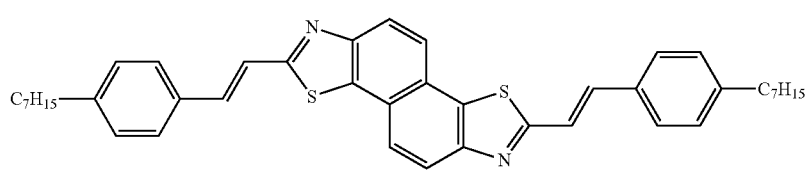
Compound 67

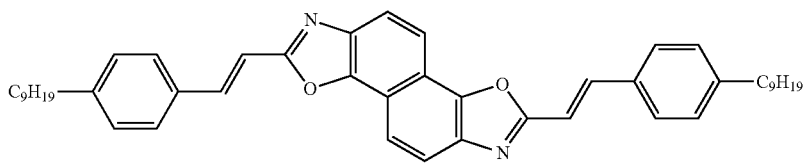

Compound 68

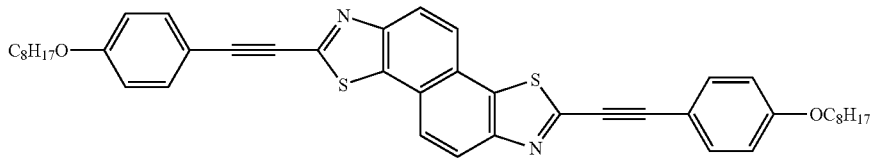

Compound 69

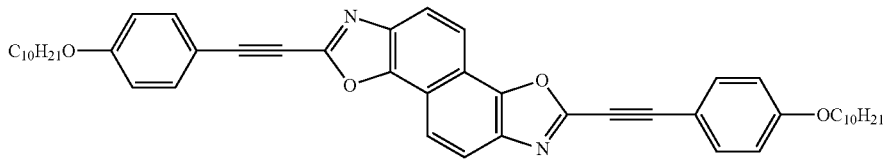

Compound 70

The compound represented by the formula (1-1) or (1-2) preferably has a molecular weight of 3,000 or less, more preferably 2,000 or less, further preferably 1,000 or less, and particularly preferably 850 or less. The molecular weight that is the upper limit or less is preferred since the compound has increased solubility in a solvent.

The molecular weight of the compound is preferably 400 or more, more preferably 450 or more, and further preferably 500 or more, from the standpoint of the stability of the film quality of the thin film.

The compound represented by the formula (1-1) or (1-2) may be synthesized by combining the known reactions. For example, the compound may be synthesized with reference to JP-A-2012-184218 and the like.

In the reaction of forming a naphthothiazole ring or a naphthoxazole ring in the invention, any reaction condition may be used. The reaction solvent used may be any solvent. An acid or a base is preferably used for promoting the ring-forming reaction, and particularly a base is preferably used. The optimum reaction condition may vary depending on the structure of the target naphthothiazole or naphthoxazole derivative, and may be determined with reference to the specific reaction shown in the aforementioned literature.

The synthesis intermediates having the various substituents may be synthesized by combining known reactions. The substituents may be introduced in any stage of the intermediates. The intermediates after synthesis are preferably purified by column chromatography, recrystallization or the like, and then purified by sublimation. The sublimation purification not only isolates organic impurities, but also effectively removes an inorganic salt, a residual solvent and the like.

Structure of Organic Thin Film Transistor

The organic thin film transistor of the invention has a semiconductor active layer that contains the compound represented by the formula (1-1) or (1-2).

The organic thin film transistor of the invention may further contain other layers in addition to the semiconductor active layer.

The organic thin film transistor of the invention is preferably used as an organic field effect transistor (FET), and is more preferably used as an insulated gate FET, in which the gate and the channel are insulated from each other.

Preferred embodiments of the organic thin film transistor of the invention will be described below with reference to the drawings, but the invention is not limited to the embodiments.

Laminated Structure

The laminated structure of the organic field effect transistor is not particularly limited, and various known structures may be used.

One example of the structure of the organic thin film transistor of the invention is a bottom-gate top-contact structure having a substrate as the lowermost layer having disposed thereon an electrode, an insulating layer, a semiconductor active layer (organic semiconductor layer), and two electrodes, in this order. In this structure, the electrode on the upper surface of the substrate as the lowermost layer is provided on a part of the substrate, and the insulating layer is disposed to be in contact with the substrate in the portion other than the electrode. The two electrodes disposed on the upper surface of the semiconductor active layer are disposed to be separated from each other.

A structure of a bottom-gate top-contact device is shown in FIG. 1. FIG. 1 is a schematic illustration showing a cross sectional structure of one example of the organic thin film transistor of the invention. The organic thin film transistor shown in FIG. 1 has a substrate 11 disposed as the lowermost layer, an electrode 12 disposed on a part of the upper surface of the substrate 11, and an insulating layer 13 disposed to cover the electrode 12 and to be in contact with the substrate 11 in the portion other than the electrode 12. A semiconductor active layer 14 is provided on the upper surface of the insulating layer 13, and two electrodes 15a and 15b, which are separated from each other, are disposed on parts of the semiconductor active layer 14.

In the organic thin film transistor shown in FIG. 1, the electrode 12 is a gate, and the electrodes 15a and 15b each are a drain or a source. The organic thin film transistor shown in FIG. 1 is an insulated gate FET, in which the channel, which is an electric current path between the drain and the source, and the gate are insulated from each other.

Another example of the structure of the organic thin film transistor of the invention is a bottom-gate bottom-contact device.

Figure 2:
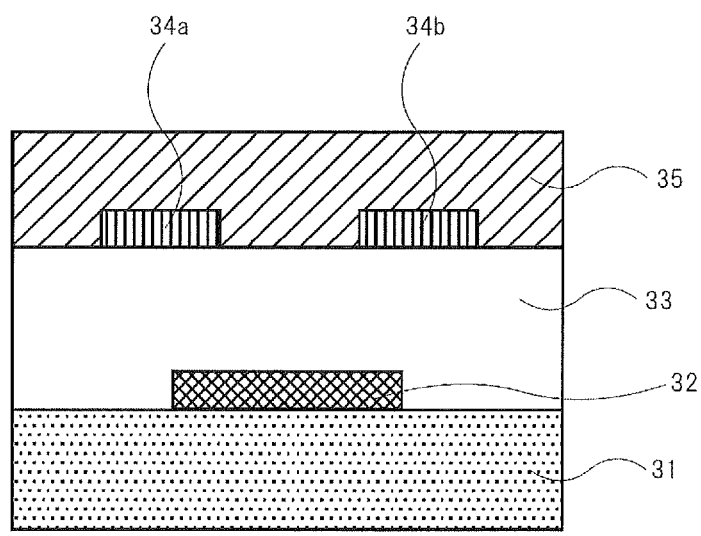
FIG. 2 is a schematic illustration showing a cross sectional structure of an organic thin film transistor that is produced as a substrate for measuring FET characteristics in the example of the invention.

A structure of a bottom-gate bottom-contact device is shown in FIG. 2. FIG. 2 is a schematic illustration showing a cross sectional structure of an organic thin film transistor that is produced as a substrate for measuring FET characteristics in the example of the invention. The organic thin film transistor shown in FIG. 2 has a substrate 31 disposed as the lowermost layer, an electrode 32 disposed on a part of the upper surface of the substrate 31, and an insulating layer 33 disposed to cover the electrode 32 and to be in contact with the substrate 31 in the portion other than the electrode 32. A semiconductor active layer 35 is provided on the upper surface of the insulating layer 33, and two electrodes 34a and 34b are disposed under the semiconductor active layer 35.

In the organic thin film transistor shown in FIG. 2, the electrode 32 is a gate, and the electrodes 34a and 34b each are a drain or a source. The organic thin film transistor shown in FIG. 2 is an insulated gate FET, in which the channel, which is an electric current path between the drain and the source, and the gate are insulated from each other.

Other preferred examples of the structure of the organic thin film transistor of the invention include a top-gate top-contact device and a top-gate bottom-contact device, in which an insulator and a gate electrode are disposed on an organic semiconductor layer.

Thickness

The organic thin film transistor of the invention preferably has a total thickness of the transistor, for example, of from 0.1 to 0.5 μm, in the case where a thinner transistor is demanded.

Sealing

For shielding the organic thin film transistor device from the air and water to enhance the storage stability of the organic thin film transistor device, the entire organic thin film transistor device may be sealed with a metallic sealing canister, an inorganic material, such as glass and silicon nitride, a polymer material, such as parylene, a low molecular weight material, and the like.

Preferred embodiments of the layers of the organic thin film transistor of the invention will be described below, but the invention is not limited to the embodiments.

Substrate

Material

The organic thin film transistor of the invention preferably contains a substrate.

The material for the substrate is not particularly limited, and known materials may be used. Examples of the material include a polyester film, such as polyethylene naphthoate (PEN) and polyethylene terephthalate (PET), a cycloolefin polymer film, a polycarbonate film, a triacetyl cellulose (TAC) film, a polyimide film, these polymer films having an ultrathin glass layer laminated thereon, ceramics, silicone, quartz, glass, and the like, and silicone is preferred.

Electrode

Material

The organic thin film transistor of the invention preferably contains an electrode.

Examples of the material for the electrode include known electroconductive materials, for example, a metal material, such as Cr, Al, Ta, Mo, Nb, Cu, Ag, Au, Pt, Pd, In, Ni and Nd, an alloy material of the metal materials, a carbon material, and an electroconductive polymer, which may be used without particular limitation.

Thickness

The thickness of the electrode is not particularly limited and is preferably from 10 to 50 nm.

The gate width (or the channel width) W and the gate length (or the channel length) L are not particularly limited, and the ratio W/L is preferably 10 or more, and more preferably 20 or more.

Insulating Layer

Material

The material for the insulating layer is not particularly limited as far as the necessary insulating effect is obtained, and examples thereof include silicon dioxide, silicon nitride, a fluorine polymer insulating material, such as PTFE and CYTOP, a polyester insulating material, a polycarbonate insulating material, an acrylic polymer insulating material, an epoxy resin insulating material, a polyimide insulating material, a polyvinylphenol resin insulating material, and a poly-p-xylylene resin insulating material.

The upper surface of the insulating layer may be surface-treated, and preferred examples thereof used include an insulating layer formed of silicon dioxide, the surface of which is surface-treated by coating hexamethyldisilazane (HMDS) or octadecyltrichlorosilane (OTS) thereon.

Thickness

The thickness of the insulating layer is not particularly limited, and in the case where a thin insulating layer is demanded, the thickness thereof is preferably from 10 to 400 nm, more preferably from 20 to 200 nm, and particularly preferably from 50 to 200 nm.

Semiconductor Active Layer

Material

The organic thin film transistor of the invention contains the compound represented by the formula (1-1) or (1-2) in the semiconductor active layer.

The semiconductor active layer may be a layer that is formed of the compound of the invention, or a layer containing a polymer binder described later in addition to the compound of the invention. The semiconductor active layer may contain a residual solvent used on forming the film.

The content of the polymer binder in the semiconductor active layer is not particularly limited, and the polymer binder is preferably used in a range of from 0 to 95% by mass, more preferably used in a range of from 10 to 90% by mass, further preferably used in a range of from 20 to 80% by mass, and particularly preferably used in a range of from 30 to 70% by mass.

Thickness

The thickness of the semiconductor active layer is not particularly limited, and in the case where a thin semiconductor active layer is demanded, the thickness thereof is preferably from 10 to 400 nm, more preferably from 10 to 200 nm, and particularly preferably from 10 to 100 nm.

Organic Semiconductor Material for Non-light Emitting Organic Semiconductor Device The invention also relates to an organic semiconductor material for a non-light emitting organic semiconductor device containing the compound represented by the formula (1-1) or (1-2).

Non-light Emitting Organic Semiconductor Device

The non-light emitting organic semiconductor device referred herein means a device that is not intended to emit light. The non-light emitting organic semiconductor device is preferably a non-light emitting organic semiconductor device that uses an electronic element having a layer structure of thin films. The non-light emitting organic semiconductor device encompasses an organic thin film transistor, an organic photoelectric conversion device (such as a solid state imaging device for a photosensor, and a solar cell for energy conversion), a gas sensor, an organic rectifying device, an organic inverter, an information recording device, and the like. The organic photoelectric conversion device may be used for both a photosensor (i.e., a solid state imaging device) and energy conversion (i.e., a solar cell). Preferred examples of the device include an organic photoelectric conversion device and an organic thin film transistor, and more preferred examples thereof include an organic thin film transistor. Accordingly, the organic semiconductor material for a non-light emitting organic semiconductor device of the invention is preferably a material for an organic thin film transistor as described above.

Organic Semiconductor Material

The organic semiconductor material referred herein means an organic material that shows characteristics of a semiconductor. The organic semiconductor material includes a p-type (hole transporting) organic semiconductor, which shows conductivity with holes as a carrier, and an n-type (electron transporting) organic semiconductor, which shows conductivity with electrons as a carrier, as similar to a semiconductor material formed of an inorganic material.

The compound of the invention may be used as any of a p-type organic semiconductor material and an n-type organic semiconductor material, and is preferably used as a p-type organic semiconductor material. The flowability of a carrier in an organic semiconductor is shown by a carrier mobility $\mu$. The carrier mobility $\mu$ is preferably as large as possible, and is preferably $1\times10^{-2}$ cm$^2$/Vs or more, more preferably $5\times10^{-2}$ CM$^2$/Vs or more, particularly preferably $1\times10^{-1}$ cm$^2$/Vs or more, further particularly preferably $5\times10^{-1}$ cm$^2$/Vs or more, and still further particularly preferably 1 cm$^2$/Vs or more. The carrier mobility $\mu$ may be obtained from the characteristics of a field effect transistor (FET) device produced or by a time-of-flight (TOF) measurement method.

Organic Semiconductor Thin Film for Non-light Emitting Organic Semiconductor Device Material The invention also relates to an organic semiconductor thin film for a non-light emitting organic semiconductor device containing the compound represented by the formula (1-1) or (1-2).

The organic semiconductor thin film for a non-light emitting organic semiconductor device of the invention contains the compound represented by the formula (1-1) or (1-2), and an embodiment thereof that contains no polymer binder is also preferred.

The organic semiconductor thin film for a non-light emitting organic semiconductor device of the invention may contain the compound represented by the formula (1-1) or (1-2) and a polymer binder.

Examples of the polymer binder include an insulating polymer, such as polystyrene, polycarbonate, polyarylate, polyester, polyamide, polyimide, polyurethane, polysiloxane, polysulfone, polymethyl methacrylate, polymethyl acrylate, cellulose, polyethylene and polypropylene, copolymers thereof, a photoconductive polymer, such as polyvinylcarbazole and polysilane, and an electroconductive polymer and a semiconductor polymer, such as polythiophene, polypyrrole, polyaniline and poly-p-phenylenevinylene.

The polymer binder may be used solely or as a combination of plural kinds thereof.

The organic semiconductor material and the polymer binder may be uniformly mixed, or a part or the whole thereof may be phase-separated, and from the standpoint of the charge mobility, such a structure that the organic semiconductor and the binder are phase-separated in the thickness direction in the film is most preferred since the charge migration of the organic semiconductor may not be inhibited by the binder.

Taking the mechanical strength of the thin film into consideration, a polymer binder having a high glass transition temperature is preferred, and taking the charge mobility into consideration, a polymer binder having a structure that contains no polar group, a photoconductive polymer, and an electroconductive polymer are preferred.

The amount of the polymer binder used is not particularly limited, and the polymer binder may be preferably used in a range of from 0 to 95% by mass, more preferably used in a range of from 10 to 90% by mass, further preferably used in a range of from 20 to 80% by mass, and particularly preferably used in a range of from 30 to 70% by mass, in the organic semiconductor thin film for a non-light emitting organic semiconductor device of the invention.

In the invention, an organic thin film having good film quality may be obtained by using the compound having the aforementioned structure. Specifically, the compound of the invention has good crystallinity to enable formation of a film having a sufficient thickness, and thus the organic semiconductor thin film for a non-light emitting organic semiconductor device of the invention thus obtained may have good quality.

Film Forming Method

The compound of the invention may be formed as a film on a substrate by any method.

On forming the film, the substrate may be heated or cooled, and the film quality and the molecular packing in the film may be controlled by changing the temperature of the substrate. The temperature of the substrate is not particularly limited, and is preferably in a range of from 0 to 200° C., more preferably in a range of from 15 to 100° C., and particularly preferably in a range of from 20 to 95° C.

On forming a film of the compound of the invention on a substrate, the film may be formed by a vacuum process or a solution process, both of which are preferred.

Specific examples of the film formation by a vacuum process include a physical vapor phase growing method, such as a vacuum vapor deposition method, a sputtering method, an ion plating method and a molecular beam epitaxy (MBE) method, and a chemical vapor deposition (CVD) method, such as plasma polymerization, and a vacuum vapor deposition method is preferably used.

The film formation by a solution process means a method, in which an organic compound is dissolved in a solvent capable of dissolving the same, and a film is formed by using the resulting solution. Specific examples thereof used include ordinary methods, for example, a coating method, such as a casting method, a dip coating method, a die coater method, a roll coater method, a bar coater method and a spin coating method, a printing method, such as an ink-jet method, a screen printing method, a gravure printing method, a flexography printing method, an offset printing method and a microcontact printing method, and a Langmuir-Blodgett (LB) method, and a casting method, a spin coating method, an ink-jet method, a gravure printing method, a flexography printing method, an offset printing method and a microcontact printing method are particularly preferably used.

The organic semiconductor thin film for a non-light emitting organic semiconductor device of the invention is preferably produced by a solution coating method. In the case where the organic semiconductor thin film for a non-light emitting organic semiconductor device of the invention contains a polymer binder, the thin film is preferably formed such a method that the material for forming the layer and the polymer binder are dissolved or dispersed in a suitable solvent to prepare a coating liquid, which is then coated by various coating methods to form the thin film.

The coating solution for a non-light emitting organic semiconductor device of the invention capable of being used for film formation by a solution process will be described below.

Coating Solution for Non-light Emitting Organic Semiconductor Device

The invention also relates to a coating solution for a non-light emitting organic semiconductor device containing the compound represented by the formula (1-1) or (1-2).

In the case where the film is formed on a substrate by a solution process, the material for forming the layer may be dissolved or dispersed in a suitable organic solvent (for example, a hydrocarbon solvent, such as hexane, octane, decane, toluene, xylene, mesitylene, ethylbenzene, decalin and 1-methylnaphthalene, a ketone solvent, such as acetone, methyl ethyl ketone, methyl isobutyl ketone and cyclohexanone, a halogenated hydrocarbon solvent, such as dichloromethane, chloroform, tetrachloromethane, dichloroethane, trichloroethane, tetrachloroethane, chlorobenzene, dichlorobenzene and chlorotoluene, an ester solvent, such as ethyl acetate, butyl acetate and amyl acetate, an alcohol solvent, such as methanol, propanol, butanol, pentanol, hexanol, cyclohexanol, methyl cellosolve, ethyl cellosolve and ethylene glycol, an ether solvent, such as dibutyl ether, tetrahydrofuran, dioxane and anisole, an amide or imide solvent, such as N,N-dimethylformamide, N,N-dimethylacetamide, 1-methyl-2-pyrrolidone and 1-methyl-2-imidazolidinone, a sulfoxide solvent, such as dimethylsulfoxide, and a nitrile solvent, such as acetonitrile) and/or water to prepare a coating liquid, which may be then coated by various coating methods to form the thin film. The solvent may be used solely or as a combination of plural kinds thereof. Among these, a hydrocarbon solvent, a halogenated hydrocarbon solvent and an ether solvent are preferred, toluene, xylene, mesitylene, tetralin, dichlorobenzene and anisole are more preferred, and toluene, xylene, tetralin and anisole are particularly preferred. The concentration of the compound represented by the formula (1-1') or (1-2') in the coating liquid is preferably from 0.1 to 80% by mass, more preferably from 0.1 to 10% by mass, and particularly preferably from 0.5 to 10% by mass, by which a film having an arbitrary thickness may be formed.

For forming a film by a solution process, it is necessary to dissolve the materials in the aforementioned solvent, but it is insufficient that the materials are simply dissolved in the solvent. In general, a material to be formed into a film by a vacuum process may be dissolved in a solvent in a certain extent. However, the solution process includes a step of evaporating the solvent to form a thin film, after coating the materials dissolved in a solvent, and most of materials that are not suitable for forming a film by a solution process have high crystallinity, and thus may be disadvantageously crystallized (agglomerated) in the step to fail to provide a favorable thin film. The compound represented by the formula (1-1) or (1-2) is advantageous also in such a point that the compound may not cause the disadvantageous crystallization (agglomeration).

As the coating solution for a non-light emitting organic semiconductor device of the invention, such an embodiment is also preferred that contains the compound represented by the formula (1-1) or (1-2), and contains no polymer binder.

The coating solution for a non-light emitting organic semiconductor device of the invention may contain the compound represented by the formula (1-1) or (1-2) and a polymer binder. In this case, the thin film may be formed in such a manner that the material for forming the layer and the polymer binder are dissolved or dispersed in the suitable solvent described above to prepare a coating liquid, which is then coated by various coating method to form the thin film. The polymer binder may be selected from those described above.

EXAMPLE

The features of the invention will be described more specifically with reference to examples and comparative examples below. The materials, the amounts used, the ratios, the contents of processes, the procedures of processes, and the like shown in the examples may be appropriately changed unless they deviate the substance of the invention. Accordingly, the scope of the invention is not construed as being limited to the following examples.

Example 1

Synthesis Example 1: Synthesis of Compound 13

The compound 13 as the compound represented by the formula (1-1) or (1-2) was synthesized by the specific synthesis procedures shown by the following scheme.

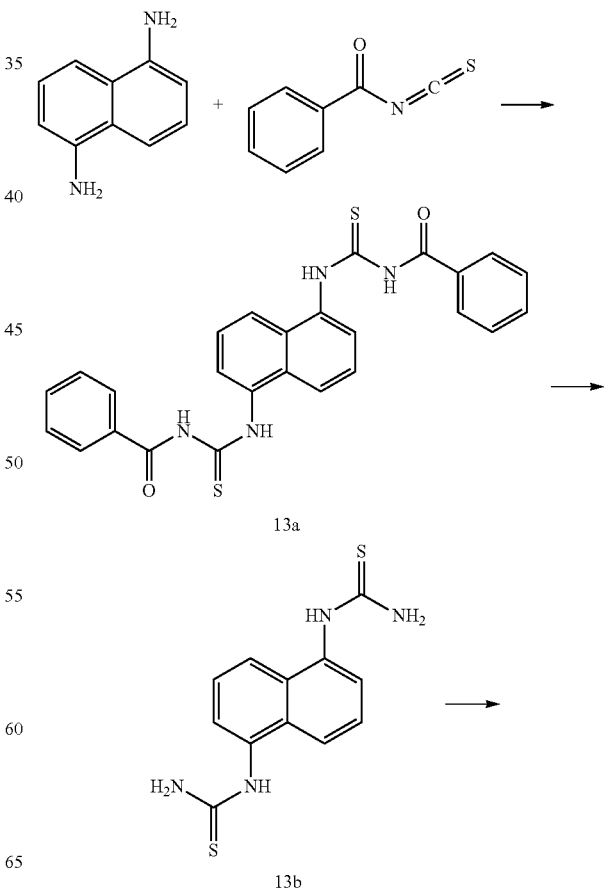

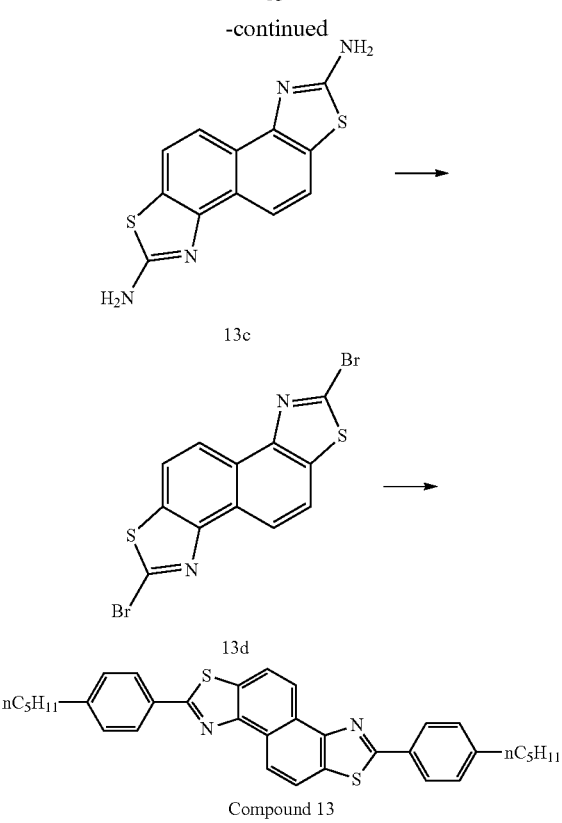

Compound 13

Synthesis of Compound 13a

A THF solution (100 mL) of benzoyl isothiocyanate (23 g) was added dropwise to a THF solution (200 mL) of 1,5-diaminonaphthalene (10 g) under cooling with ice, and the mixture was stirred for 1 hour. The reaction liquid was concentrated under reduced pressure, and the resulting crude crystals were recrystallized to provide a compound 13a (30.3 g).

Synthesis of Compound 13b

Methanol (380 mL) and water (95 mL) were added to the compound 13a (25.3 g) and sodium hydroxide (62.6 g), and the mixture was stirred at room temperature for 12 hours. The reaction liquid was concentrated under reduced pressure, and the residue after the concentration was rinsed with methanol to provide a compound 13b (10.1 g).

Synthesis of Compound 13c

Bromine (3.7 mL) was added dropwise to a chloroform solution (70 mL) of the compound 13c (10 g) under cooling with ice, and the mixture was stirred under heating to reflux for 3 hours. The solid matter thus deposit was collected by filtering, rinsed with chloroform, and then further rinsed with a sodium hydrogen sulfite aqueous solution to provide a compound 13c (9.1 g).

Synthesis of Compound 13d

Copper (II) bromide (7.9 g) was stirred at 100° C. for 1 hour, to which acetonitrile (220 mL) and polyethylene glycol 200 (7.3 g) were added at room temperature, and the mixture was stirred for 30 minutes. After adding isoamyl nitrite (3.0 mL) dropwise thereto, an N,N-dimethylacetamide solution (200 mL) of the compound 13c (2 g) was added dropwise thereto, and the mixture was stirred for 2 hours. The reaction liquid was poured into a 1N hydrochloric acid aqueous solution, and the resulting solid matter was collected by filtration. The collected matter was dissolved in chloroform, the resulting solution was filtered with Celite, and the filtrate was concentrated under reduced pressure. The residue after the concentration was purified by column chromatography to provide a compound 13d (1.9 g).

Synthesis of Compound 13

THF (400 mL) and water (80 mL) were added to the compound 13d (1.2 g), 4-penthylphenylboric acid (1.7 g), 2-dicyclohexylphosphino-2', 6'-dimethoxybiphenyl (SPhos) (0.3 g) and potassium phosphate (3.2 g), to which tris (dibenzylideneacetone) dipalladium $(Pd_2(dba)_3)$ (0.27 g) was added, and then the mixture was stirred in a nitrogen atmosphere under heating to reflux for 3 hours. The reaction liquid was filtered with Celite and separated into an organic layer and an aqueous layer. The organic layer was washed with a sodium chloride aqueous solution, dried over magnesium sulfate, and then concentrated under reduced pressure. The resulting coarse crystals were repeatedly recrystallized from THF/ethanol to provide the compound 13 (0.95 g). The compound thus obtained was identified by elemental analysis, NMR and mass spectrum. The result of identification of the compound 13 by $^1$H-NMR is shown below.

d-$CDCl_3$: 8.92 (2H), 8.18-8.10 (3H), 7.38-7.32 (3H), 2.75-2.68 (4H), 1.76-1.68 (4H), 1.46-1.30 (8H), 0.99-0.90 (6H)

Figure 3:
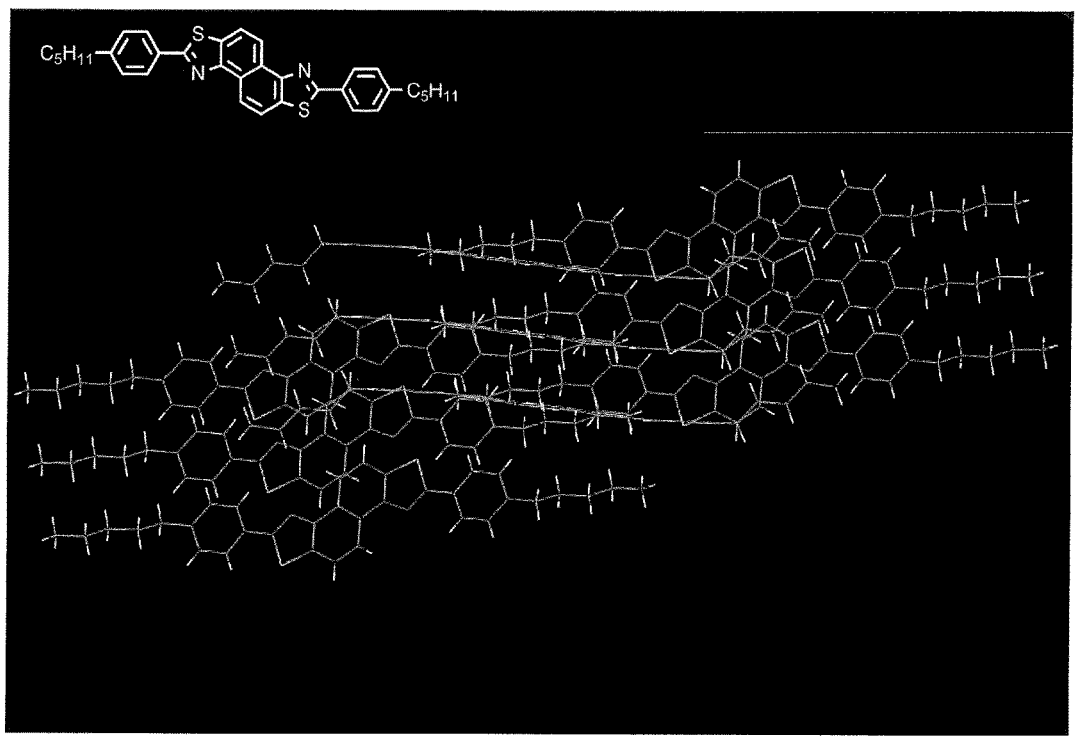
FIG. 3 shows the X-ray crystal analysis data (i.e., the diagram of the unit crystal lattice) of the compound 13.

The crystals of the compound 13 having been purified by sublimation were subjected to single crystal X-ray structure analysis. The resulting X-ray crystallography data (unit crystal lattice) is shown in FIG. 3.

The other compounds represented by the formula (1-1) or (1-2) were synthesized in the similar manner as for the compound 13.

The result of identification of the compound 1A by $^1$H-NMR is shown below.

d-$CDCl_3$: 8.80-8.72 (2H), 8.08-8.02 (2H), 2.02-1.92 (4H), 1.51-1.25 (12H), 0.99-0.90 (6H)

Comparative compounds 1 to 5 used in a semiconductor active layer (organic semiconductor layer) of comparative devices were synthesized according to the methods described in the literatures. The structures of the comparative compounds 1 to 5 are shown below.

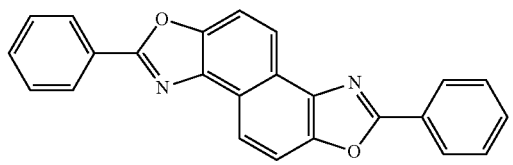

Comparative Compound 1 described in
JP-A-5-214335

-continued

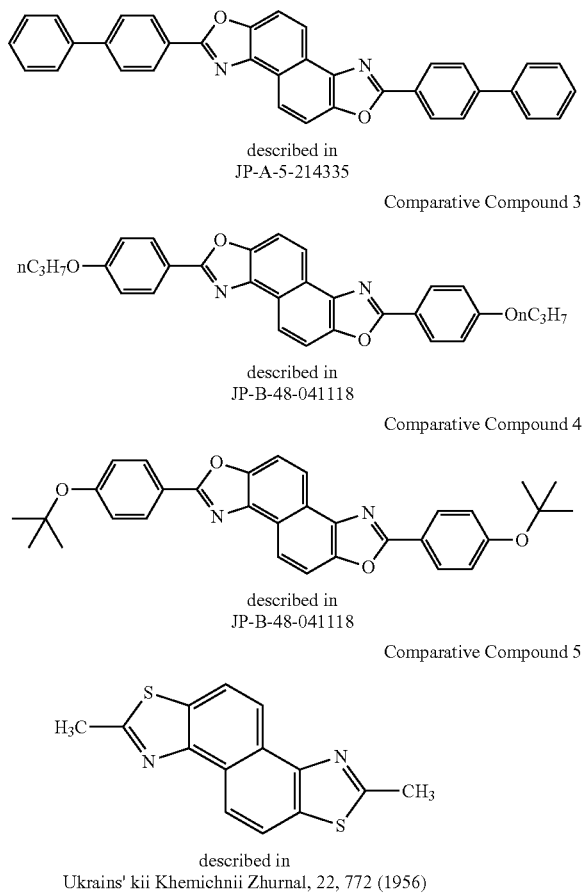

Comparative Compound 2
described in JP-A-5-214335

Comparative Compound 3
described in JP-B-48-041118

Comparative Compound 4
described in JP-B-48-041118

Comparative Compound 5
described in Ukrains' kii Khemichnii Zhurnal, 22, 772 (1956)

Production and Evaluation of Devices

All the materials used for producing devices were purified by sublimation, and were confirmed to have a purity (absorption intensity area ratio at 254 nm) of 99.5% or more by high-performance liquid chromatography (TSKgel ODS-100Z, available from Tosoh Corporation).

Example 2

Formation of Semiconductor Active Layer (Organic Semiconductor Layer) only with Compound The compound of the invention or the comparative compound (1 mg each) and toluene (1 mL) were mixed and heated to 100° C. to prepare a coating solution for a non-light emitting organic semiconductor device. The coating solution was cast on a substrate for measuring FET characteristics heated to 90° C. under nitrogen atmosphere to form an organic semiconductor thin film for a non-light emitting organic semiconductor device, thereby providing an organic thin film transistor device of Example 2 for measuring FET characteristics. The substrate for measuring FET characteristics used was a silicon substrate having a bottom-gate bottom-contact structure having chromium/gold electrodes (gate width W=100 mm, gate length L=100 μm) disposed in an interdigitated form as source and drain electrodes, and $SiO_2$ (thickness: 200 nm) as an insulating film (the schematic structural illustration shown in FIG. 2).

The FET characteristics of the organic thin film transistor device of Example 2 were evaluated in terms of the carrier mobility and the change in the threshold voltage after repeated driving by using a semiconductor parameter analyzer (4156C, produced by Agilent Technologies, Inc.) having a semi-automatic prober (AX-2000, produced by Vector Semiconductor Co., Ltd.) connected thereto under a normal pressure nitrogen atmosphere.

The results obtained are shown in Table 1 below.

(a) Carrier Mobility

While applying a voltage of −80 V between the source electrode and the drain electrode of the organic thin film transistor device (FET device), the gate voltage was changed within a range of from 20 to −100 V, and the carrier mobility μ was calculated by the following expression showing the drain current $I_d$.

$$I_d = (W/2L)\mu C_i (V_g - V_{th})^2$$

wherein L represents the gate length, W represents the gate width, $C_i$ represents the capacity of the insulating layer per unit area, $V_g$ represents the gate voltage, and $V_{th}$ represents the threshold voltage. A device that exhibited a carrier mobility of less than $1 \times 10^{-5}$ cm$^2$/Vs was not subjected to the subsequent evaluation of (b) the change in the threshold voltage after repeated driving due to the too poor property thereof.

(b) Change in Threshold Voltage after Repeated Driving

While applying a voltage of −80 V between the source electrode and the drain electrode of the organic thin film transistor device (FET device), the gate voltage was changed 100 times within a range of from 20 to −100 V, and the same measurement as in the measurement (a) above to evaluate the difference ($|V_1 - V_0|$) between the threshold voltage $V_0$ before repeated driving and the threshold voltage $V_1$ after repeated driving according to the following three grades. A smaller value thereof shows higher repeated driving stability of the device and thus is preferred. The change in the threshold voltage after repeated driving is preferably the grade A for practical use.

A: $|V_1 - V_0| \leq 5$ V
B: $5 < |V_1 - V_0| \leq 10$ V
C: $|V_1 - V_0| > 10$ V

TABLE 1

| Device No. | Organic semiconductor material | Carrier mobility (cm$^2$/Vs) | Change in threshold voltage after repeated driving | Note |
|---|---|---|---|---|
| Device 1 | Compound 5 | $3 \times 10^{-1}$ | A | invention |
| Device 2 | Compound 8 | $5 \times 10^{-1}$ | A | invention |
| Device 3 | Compound 9 | $6 \times 10^{-1}$ | A | invention |
| Device 4 | Compound 10 | $2 \times 10^{-1}$ | A | invention |
| Device 5 | Compound 11 | $4 \times 10^{-1}$ | A | invention |
| Device 6 | Compound 13 | $8 \times 10^{-2}$ | A | invention |
| Device 7 | Compound 14 | $1 \times 10^{-1}$ | A | invention |
| Device 8 | Compound 17 | $2 \times 10^{-1}$ | A | invention |
| Device 9 | Compound 19 | $1 \times 10^{-1}$ | A | invention |
| Device 10 | Compound 20 | $9 \times 10^{-2}$ | A | invention |
| Device 11 | Compound 21 | $5 \times 10^{-1}$ | A | invention |
| Device 12 | Compound 27 | $1 \times 10^{-1}$ | A | invention |
| Device 13 | Compound 33 | $5 \times 10^{-2}$ | A | invention |
| Device 14 | Compound 34 | $6 \times 10^{-2}$ | A | invention |
| Device 15 | Compound 40 | $4 \times 10^{-2}$ | A | invention |
| Device 16 | Compound 41 | $4 \times 10^{-1}$ | A | invention |
| Device 17 | Compound 46 | $8 \times 10^{-2}$ | A | invention |
| Device 18 | Compound 49 | $6 \times 10^{-1}$ | A | invention |
| Device 19 | Compound 56 | $4 \times 10^{-1}$ | A | invention |
| Device 20 | Compound 59 | $7 \times 10^{-2}$ | A | invention |
| Device 21 | Compound 61 | $4 \times 10^{-2}$ | A | invention |
| Comparative Device 1 | Comparative Compound 1 | $2 \times 10^{-2}$ | C | comparison |

TABLE 1-continued

| Device No. | Organic semiconductor material | Carrier mobility (cm$^2$/Vs) | Change in threshold voltage after repeated driving | Note |
| --- | --- | --- | --- | --- |
| Comparative Device 2 | Comparative Compound 2 | $8 \times 10^{-3}$ | C | comparison |
| Comparative Device 3 | Comparative Compound 3 | $2 \times 10^{-2}$ | B | comparison |
| Comparative Device 4 | Comparative Compound 4 | $6 \times 10^{-4}$ | A | comparison |
| Comparative Device 5 | Comparative Compound 5 | $<1 \times 10^{-5}$ | — | comparison |

It was understood from Table 1 that the organic thin film transistor devices using the compounds of the invention had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices using the comparative compounds 2, 4 and 5 had a low carrier mobility. The organic thin film transistor devices using the comparative compounds 1 to 3 and 5 had a large change in the threshold voltage after repeated driving.

Example 3

Formation of Semiconductor Active Layer (Organic Semiconductor Layer) with both Compound and Binder Organic thin film transistor devices for measuring FET characteristics were produced in the same manner as in Example 1 except for using a coating solution prepared in such a manner that the compound of the invention or the comparative compound (1 mg each), 1 mg of PaMS (poly (α-methylstyrene), Mw: 300,000, produced by Sigma-Aldrich, Inc.) and toluene (1 mL) were mixed and heated to 100° C., and then evaluated in the same manner as in Example 2.

The results obtained are shown in Table 2 below.

TABLE 2

| Device No. | Organic semiconductor material | Carrier mobility (cm$^2$/Vs) | Change in threshold voltage after repeated driving | Note |
| --- | --- | --- | --- | --- |
| Device 22 | Compound 1 | $3 \times 10^{-1}$ | A | invention |
| Device 23 | Compound 2 | $1 \times 10^{-1}$ | A | invention |
| Device 24 | Compound 6 | $9 \times 10^{-2}$ | A | invention |
| Device 25 | Compound 7 | $1 \times 10^{-1}$ | A | invention |
| Device 26 | Compound 9 | $2 \times 10^{-1}$ | A | invention |
| Device 27 | Compound 12 | $8 \times 10^{-2}$ | A | invention |
| Device 28 | Compound 15 | $3 \times 10^{-2}$ | A | invention |
| Device 29 | Compound 18 | $4 \times 10^{-2}$ | A | invention |
| Device 30 | Compound 22 | $8 \times 10^{-2}$ | A | invention |
| Device 31 | Compound 28 | $1 \times 10^{-1}$ | A | invention |
| Device 32 | Compound 42 | $2 \times 10^{-1}$ | A | invention |
| Device 33 | Compound 47 | $6 \times 10^{-2}$ | A | invention |
| Comparative Device 6 | Comparative Compound 1 | $6 \times 10^{-3}$ | B | comparison |
| Comparative Device 7 | Comparative Compound 2 | $2 \times 10^{-3}$ | B | comparison |
| Comparative Device 8 | Comparative Compound 3 | $4 \times 10^{-3}$ | A | comparison |
| Comparative Device 9 | Comparative Compound 4 | $7 \times 10^{-5}$ | A | comparison |
| Comparative Device 10 | Comparative Compound 5 | $<1 \times 10^{-5}$ | — | comparison |

It was understood from Table 2 that the organic thin film transistor devices having a semiconductor active layer formed by using the compounds of the invention along with the binder had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices having a semiconductor active layer formed by using the comparative compounds 1 to 5 along with the binder had a low carrier mobility. The organic thin film transistor devices having a semiconductor active layer formed by using the comparative compounds 1 and 2 along with the binder had a large change in the threshold voltage after repeated driving.

It was understood from the observation with an optical microscope of the organic thin film transistor devices obtained in Example 3 that the thin films using PaMS as a binder all had considerably high smoothness and uniformity of the film.

It was understood from these results that the comparative devices having a semiconductor active layer formed with the composite system of the binder and the comparative compound had a considerably low carrier mobility, whereas the organic thin film transistor devices of the invention having a semiconductor active layer formed with both the compound of the invention and the binder had a good carrier mobility, a small change in the threshold voltage after repeated driving, and considerably high smoothness and uniformity of the film.

Example 4

Formation of Semiconductor Active Layer (Organic Semiconductor Layer)

A silicon wafer having a gate insulating film of SiO$_2$ (thickness: 370 nm) was subjected to a surface treatment with octyltrichlorosilane.

The compound of the invention or the comparative compound (1 mg each) and toluene (1 mL) were mixed and heated to 100° C. to prepare a coating solution for a non-light emitting organic semiconductor device. The coating solution was cast on the octyltrichlorosilane-treated silicon wafer heated to 90° C. to form an organic semiconductor thin film for a non-light emitting organic semiconductor device.

On the surface of the thin film thus formed, gold was vapor-deposited through a mask to form source and drain electrodes, thereby providing an organic thin film transistor device having a bottom-gate top-contact structure having a gate width W of 5 mm and a gate length L of 80 μm (the schematic structural illustration shown in FIG. 1).

The FET characteristics of the organic thin film transistor device of Example 4 were evaluated in terms of the carrier mobility and the change in the threshold voltage after repeated driving by using a semiconductor parameter analyzer (4156C, produced by Agilent Technologies, Inc.) having a semi-automatic prober (AX-2000, produced by Vector Semiconductor Co., Ltd.) connected thereto under a normal pressure nitrogen atmosphere.

The results obtained are shown in Table 3 below.

TABLE 3

| Device No. | Organic semiconductor material | Carrier mobility ($cm^2/Vs$) | Change in threshold voltage after repeated driving | Note |
|---|---|---|---|---|
| Device 34 | Compound 5 | 1.1 | A | invention |
| Device 35 | Compound 7 | 1.3 | A | invention |
| Device 36 | Compound 9 | 1.6 | A | invention |
| Device 37 | Compound 10 | 1.5 | A | invention |
| Device 38 | Compound 11 | 1.2 | A | invention |
| Device 39 | Compound 12 | 1.8 | A | invention |
| Device 40 | Compound 13 | $4 \times 10^{-1}$ | A | invention |
| Device 41 | Compound 19 | $2 \times 10^{-1}$ | A | invention |
| Device 42 | Compound 23 | 1.4 | A | invention |
| Device 43 | Compound 24 | 1.0 | A | invention |
| Device 44 | Compound 43 | $6 \times 10^{-1}$ | A | invention |
| Device 45 | Compound 44 | $7 \times 10^{-1}$ | A | invention |
| Device 46 | Compound 50 | $5 \times 10^{-1}$ | A | invention |
| Device 47 | Compound 51 | $4 \times 10^{-1}$ | A | invention |
| Device 48 | Compound 53 | $3 \times 10^{-1}$ | A | invention |
| Comparative Device 11 | Comparative compound 1 | $8 \times 10^{-2}$ | C | comparison |
| Comparative Device 12 | Comparative compound 2 | $5 \times 10^{-2}$ | C | comparison |
| Comparative Device 13 | Comparative compound 3 | $6 \times 10^{-2}$ | B | comparison |
| Comparative Device 14 | Comparative compound 4 | $4 \times 10^{-3}$ | A | comparison |
| Comparative Device 15 | Comparative compound 5 | $<1 \times 10^{-5}$ | — | comparison |

It was understood from Table 3 that the organic thin film transistor devices using the compounds of the invention had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices using the comparative compounds 4 and 5 had a low carrier mobility. The organic thin film transistor devices using the comparative compounds 1 to 3 had a large change in the threshold voltage after repeated driving.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2014/052218 filed on Jan. 31, 2014; Japanese Patent Application No. 2013-019583 filed on Feb. 4, 2013; and Japanese Patent Application No. 2014-015378 filed on Jan. 30, 2014, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. An organic thin film transistor containing a compound represented by the following formula (1-1) or (1-2) in a semiconductor active layer:

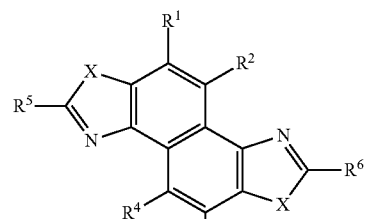

Formula (1-1)

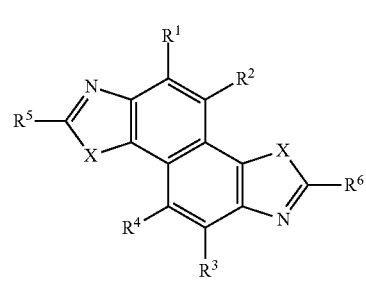

Formula (1-2)

wherein in the formulae (1-1) and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R      Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

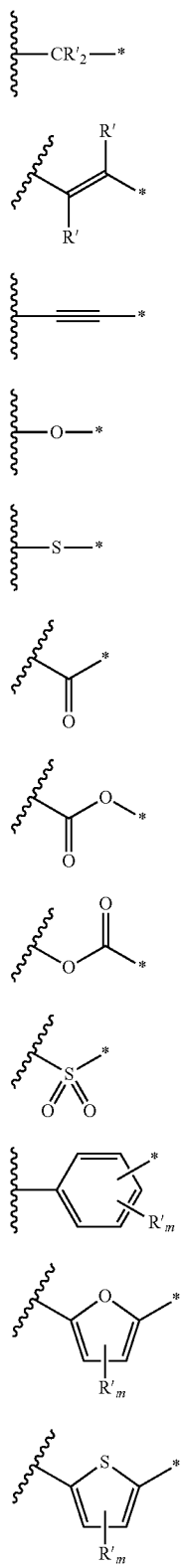

(L-1)
(L-2)
(L-3)
(L-4)
(L-5)
(L-6)
(L-7)
(L-8)
(L-9)
(L-10)
(L-11)
(L-12)

wherein in the formulae (L-1) to (L-12), the wavy line represents a position bonded to the naphthothiazole or naphthoxazole skeleton; in the formula (L-10), m represents 4, in the formulae (L-11) and (L-12), m represents 2; and in the formulae (L-1), (L-2), (L-10), (L-11) and (L-12), R' each independently represent a hydrogen atom or a substituent.

2. The organic thin film transistor according to claim 1, wherein at least one of $R^5$ and $R^6$ represents a substituent represented by the formula (W).

3. The organic thin film transistor according to claim 1, wherein the compound represented by the formula (1-1) or (1-2) is a compound represented by the following formula (2-1) or (2-2):

Formula (2-1)

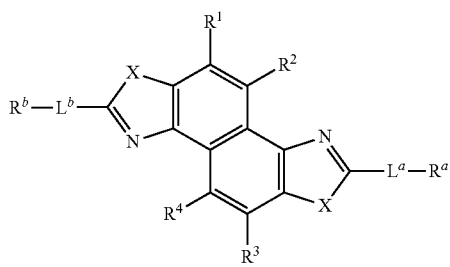

wherein in the formula (2-1), $R^1$ to $R^4$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^a$ and $R^b$ each have a number of carbon atoms in the main chain thereof of 3 or more in the case where $L^a$ and $L^b$ respectively represent a divalent linking group represented by the formula (L-1), 2 or more in the case where $L^a$ and $L^b$ respectively represent a divalent linking group represented by the formula (L-2) or (L-3), or 4 or more in the case where $L^a$ and $L^b$ respectively represent a divalent linking group represented by any one of the formulae (L-4) to (L-12), and $R^a$ and $R^b$ each represent a substituted or unsubstituted trialkylsilyl group only in the case where $L^a$ and $L^b$ adjacent to $R^a$ and $R^b$ respectively represent a divalent linking group represented by the formula (L-3), Formula (2-2)

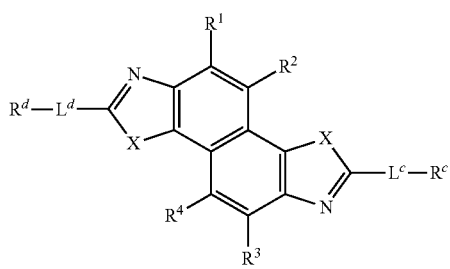

wherein in the formula (2-2), $R^1$ to $R^4$ independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^c$ and $R^d$ each have a number of carbon atoms in the main chain thereof of 3 or more in the case where $L^c$ and $L^d$ respectively represent a divalent linking group represented by the formula (L-1), 2 or more in the case where $L^c$ and $L^d$ respectively represent a divalent linking group represented by the formula (L-2) or (L-3), or 4 or more in the case where $L^c$ and $L^d$ respectively represent a divalent linking group represented by any one of the formulae (L-4) to (L-12), and $R^c$ and $R^d$ each represent a substituted or unsubstituted trialkylsilyl group only in the case where $L^c$ and $L^d$ adjacent to $R^c$ and $R^d$ respectively represent a divalent linking group represented by the formula (L-3):

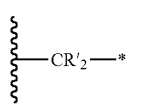
(L-1)

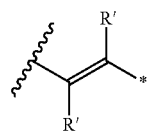
(L-2)

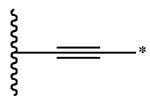
(L-3)

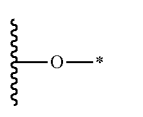
(L-4)

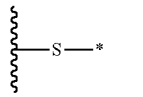
(L-5)

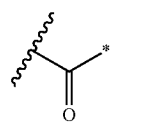
(L-6)

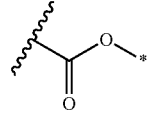
(L-7)

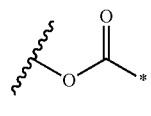
(L-8)

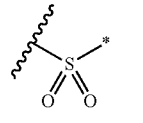
(L-9)

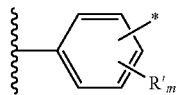
(L-10)

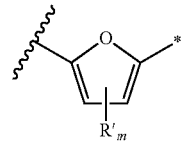
(L-11)

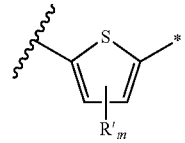
(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

4. The organic thin film transistor according to claim 1, wherein in the formula (W), R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 4 or more in the case where L represents a divalent linking group represented by any one of the formulae (L-1) and (L-4) to (L-12), or 2 or more in the case where L represents a divalent linking group represented by the formula (L-2) or (L-3), and R represents a substituted or unsubstituted trialkylsilyl group only in the case where L adjacent to R represents a divalent linking group represented by the formula (L-3).

5. The organic thin film transistor according to claim 3, wherein in the formula (2-1) or (2-2), $R^1$ to $R^4$ each independently represent a hydrogen atom, a fluorine atom, a substituted or unsubstituted alkyl group having from 1 to 12 carbon atoms, a substituted or unsubstituted alkynyl group having from 2 to 12 carbon atoms, a substituted or unsubstituted alkenyl group having from 2 to 12 carbon atoms, a substituted or unsubstituted aryl group having from 6 to 12 carbon atoms, a substituted or unsubstituted alkoxy group having from 1 to 12 carbon atoms, or a substituted or unsubstituted alkylthio group having from 1 to 12 carbon atoms.

6. The organic thin film transistor according to claim 3, wherein in the formula (2-1) or (2-2), all of $L^a$, $L^b$, $L^c$ and $L^d$ each represent a divalent linking group represented by any one of the formulae (L-1) to (L-3), (L-10), (L-11) and (L-12), or a divalent linking group containing 2 or more of the divalent linking groups bonded to each other.

7. The organic thin film transistor according to claim 3, wherein in the formula (2-1) or (2-2), all of $L^a$, $L^b$, $L^c$ and $L^d$ each represent a divalent linking group represented by the formula (L-1) or (L-10).

8. The organic thin film transistor according to claim 3, wherein in the formula (2-1) or (2-2), all $R^a$, $R^b$, $R^c$ and $R^d$ each represent a substituted or unsubstituted alkyl group.

9. The organic thin film transistor according to claim 3, wherein in the formula (2-1) or (2-2), all $R^a$, $R^b$, $R^c$ and $R^d$ each represent a linear alkyl group.

10. A compound represented by the following formula (1-1') or (1-2'):

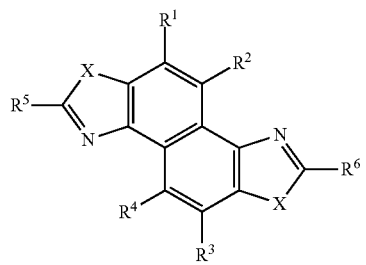

Formula (1-1')

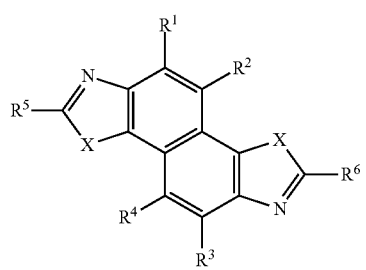

Formula (1-2')

wherein in the formulae (1-1') and (1-2'), X represents a S atom or an O atom; and $R^1$ to $R^6$ each independently represent a hydrogen atom or a substituent, provided that at least one of $R^1$ to $R^6$ represents a substituent represented by the following formula (W'):

-L-R    Formula (W')

wherein in the formula (W'), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 7 or more in the case where L represents a divalent linking group represented by the formula (L-1), 4 or more the case where L represents a divalent linking group represented by the formulae (L-4) or (L-12),or 2 or more in the where L represents a divalent linking group represented by the formula (L-2)or (L-3),and R represents a substituted or unsubstituted trialkylsilyl group only in the case where L adjacent to R represents a divalent linking group represented by the formula (L-3):

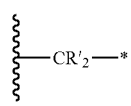

(L-1)

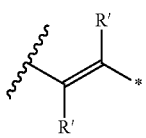

(L-2)

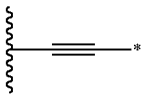

(L-3)

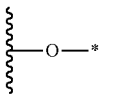

(L-4)

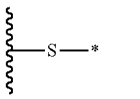

(L-5)

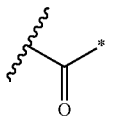

(L-6)

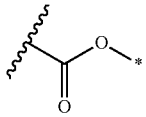

(L-7)

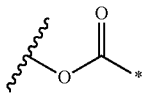

(L-8)

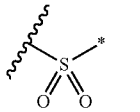

(L-9)

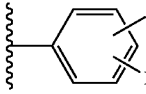

(L-10)

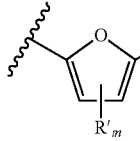

(L-11)

(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

11. The compound according to claim 10, wherein at least one of $R^5$ and $R^6$ represents a substituent represented by the formula (W).

12. The compound according to claim 10, wherein the compound represented by the formula (1-1') or (1-2') is a compound represented by the following formula (2-1') or (2-2'):

Formula (2-1')

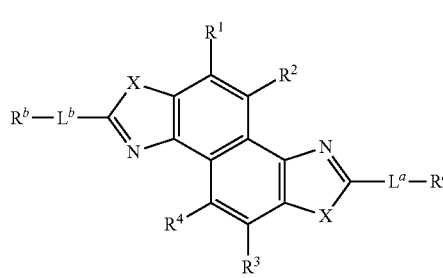

wherein in the formula (2-1'), $R^1$ to $R^4$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^a$ and $R^b$ each have a number of carbon atoms in the main chain thereof of 7 or more in the case where $L^a$ and $L^b$ respectively represent a divalent linking group represented by the formula (L-1), 4 or more in the case where $L^a$ and $L^b$ respectively represent a divalent linking group represented by any one of the formulae (L-4) to (L-12), or 2 or more in the case where $L^a$ and $L^b$ respectively represent a divalent linking group represented by the formula (L-2) or (L-3), and $R^a$ and $R^b$ each represent a substituted or unsubstituted trialkylsilyl group only in the case where $L^a$ and $L^b$ adjacent to $R^a$ and $R^b$ respectively represent a divalent linking group represented by the formula (L-3), Formula (2-2')

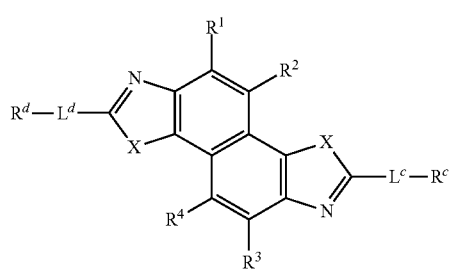

wherein in the formula (2-2'), $R^1$ to $R^4$ independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl groups represented by $R^c$ and $R^d$ each have a number of carbon atoms in the main chain thereof of 4 or more in the case where $L^c$ and $L^d$ respectively represent a divalent linking group represented by any one of the formulae (L-1) and (L-4) to (L-12), or 2 or more in the case where $L^c$ and $L^d$ respectively represent a divalent linking group represented by the formula (L-2) or (L-3), and $R^c$ and $R^d$ each represent a substituted or unsubstituted trialkylsilyl group only in the case where $L^c$ and $L^d$ adjacent to $R^c$ and $R^d$ respectively represent a divalent linking group represented by the formula (L-3):

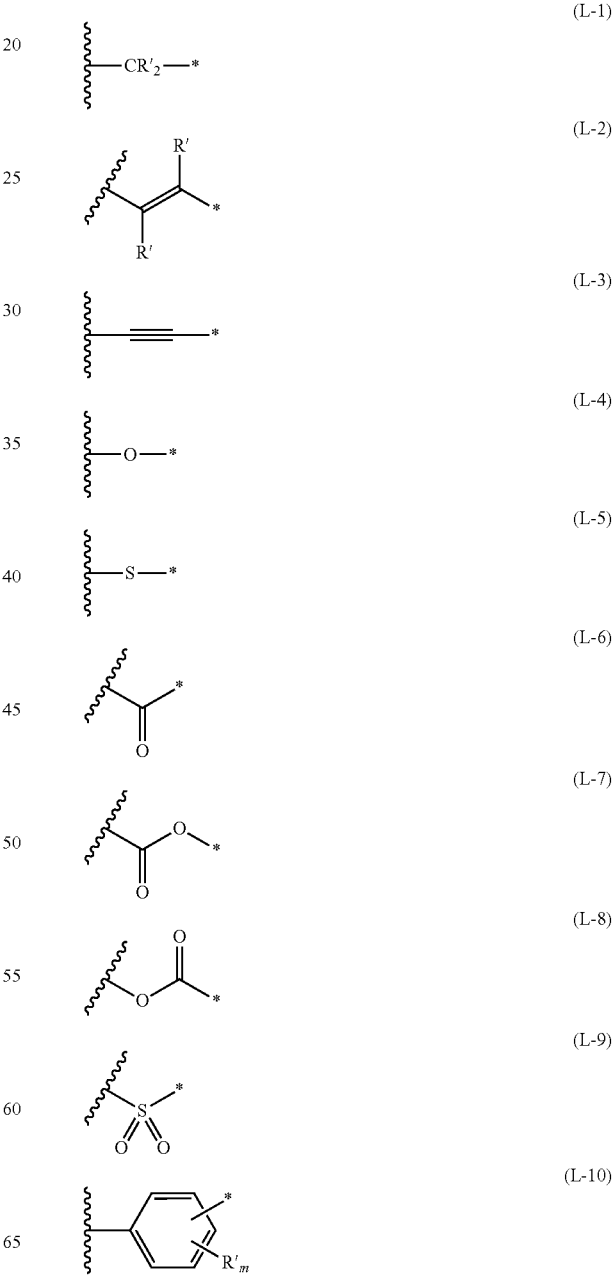

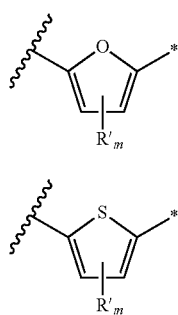

(L-11)

(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

13. The compound according to claim 12, wherein in the formula (2-1') or (2-2'), $R^1$ to $R^4$ each independently represent a hydrogen atom, a fluorine atom, a substituted or unsubstituted alkyl group having from 1 to 12 carbon atoms, a substituted or unsubstituted alkynyl group having from 2 to 12 carbon atoms, a substituted or unsubstituted alkenyl group having from 2 to 12 carbon atoms, a substituted or unsubstituted aryl group having from 6 to 12 carbon atoms, a substituted or unsubstituted alkoxy group having from 1 to 12 carbon atoms, or a substituted or unsubstituted alkylthio group having from 1 to 12 carbon atoms.

14. The compound according to claim 12, wherein in the formula (2-1') or (2-2'), all of $L^a$, $L^b$, $L^c$ and $L^d$ each represent a divalent linking group represented by any one of the formulae (L-1) to (L-3), (L-10), (L-11) and (L-12), or a divalent linking group containing 2 or more of the divalent linking groups bonded to each other.

15. The compound according to claim 12, wherein in the formula (2-1') or (2-2'), all of $L^a$, $L^b$, $L^c$ and $L^d$ each represent a divalent linking group represented by the formula (L-1) or (L-10).

16. The compound according to claim 12, wherein in the formula (2-1') or (2-2'), all $R^a$, $R^b$, $R^c$ and $R^d$ each represent a substituted or unsubstituted alkyl group.

17. The compound according to claim 12, wherein in the formula (2-1') or (2-2'), all $R^a$, $R^b$, $R^c$ and $R^d$ each represent a linear alkyl group.

18. An organic semiconductor material for a non-light emitting organic semiconductor device, containing a compound represented by the following formula (1-1) or (1-2):

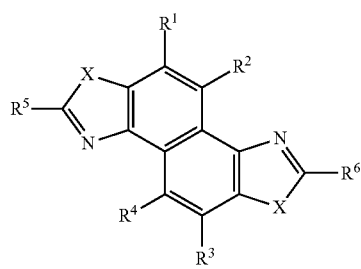

Formula (1-1)

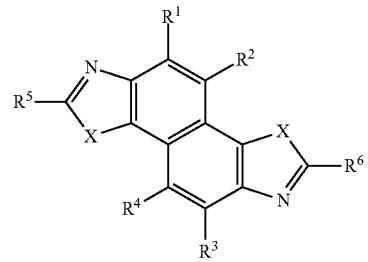

Formula (1-2)

wherein in the formulae (1-1) and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R    Formula (W)

wherein in the formula (W), L represents a divalent linking group represented by any one of the following formulae (L-1) to (L-12), or a divalent linking group containing 2 or more divalent linking groups each represented by any one of the following formulae (L-1) to(L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

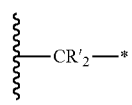 (L-1)

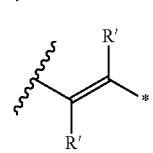 (L-2)

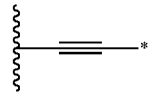 (L-3)

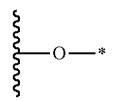 (L-4)

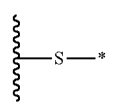 (L-5)

(L-6)

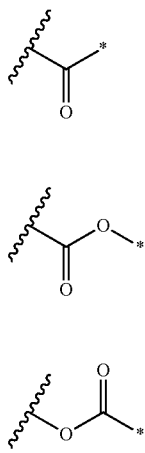

(L-7)

(L-8)

(L-9)

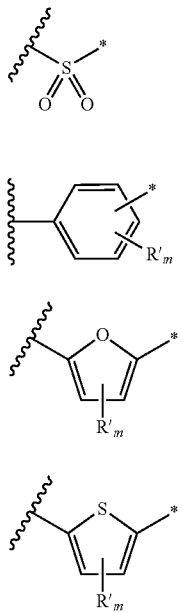

(L-10)

(L-11)

(L-12)

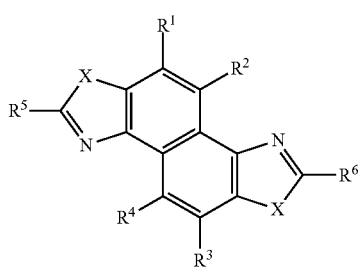

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

19. A material for an organic thin film transistor, containing a compound represented by the following formula (1-1') or (1-2):

Formula (1-1')

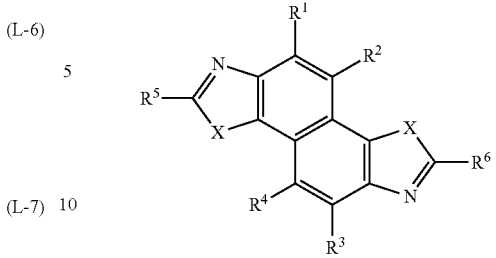

Formula (1-2)

wherein in the formulae (1-1') and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R        Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 7 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

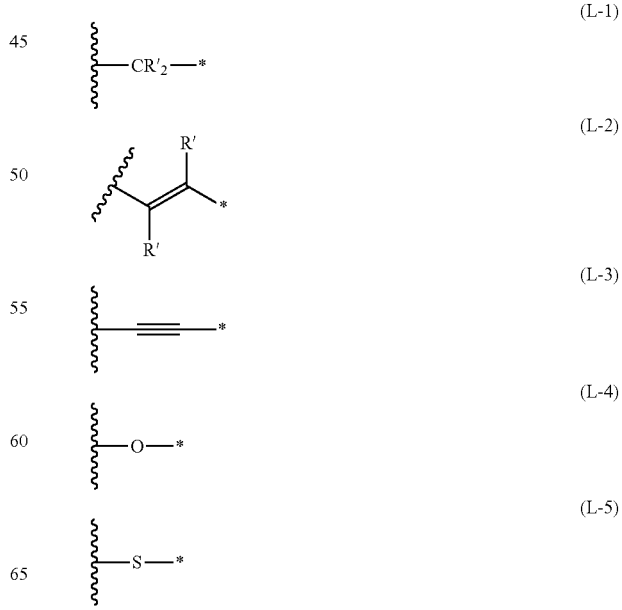

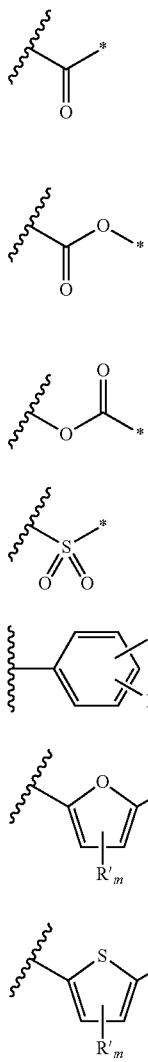

(L-6)
(L-7)
(L-8)
(L-9)
(L-10)
(L-11)
(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

20. A coating solution for a non-light emitting organic semiconductor device, containing a compound represented by the following formula (1-1') or (1-2):

Formula (1-1')

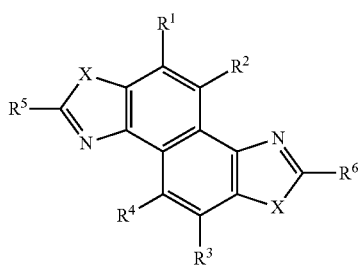

Formula (1-2)

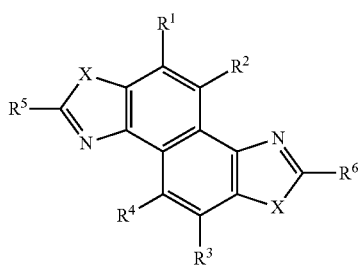

wherein in the formulae (1-1') and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R    Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 7 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

(L-1)
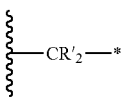

(L-2)
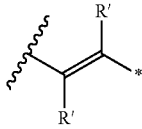

(L-3)
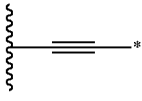

(L-4)
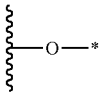

(L-5)
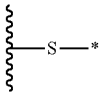

-continued (L-6)
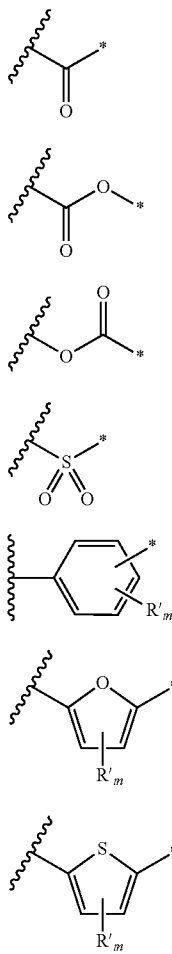

(L-7)

(L-8)

(L-9)

(L-10)

(L-11)

(L-12)

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

21. The coating solution for a non-light emitting organic semiconductor device according to claim 20, containing the compound represented by the formula (1-1') or (1-2) and a polymer binder.

22. An organic semiconductor thin film for a non-light emitting organic semiconductor device, containing a compound represented by the following formula (1-1) or (1-2):

Formula (1-1)
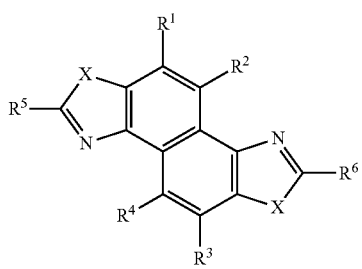

Formula (1-2)
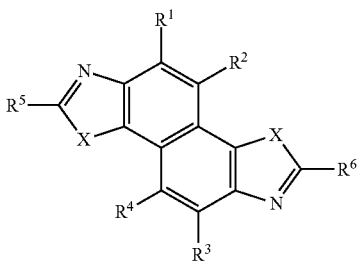

wherein in the formulae (1-1) and (1-2), X represents a S atom or an O atom; and $R^1$ to $R^6$ each independently represent a hydrogen atom or a substituent, provided that at least one of $R^1$ to $R^6$ represents a substituent represented by the following formula (W):

-L-R  Formula (W)

wherein in the formula (W), L represents a divalent linking group represented by any one of the following formulae (L-1) to (L-12), or a divalent linking group containing 2 or more divalent linking groups each represented by any one of the following formulae (L-1) to(L- 12) bonded to each other; and R represents a substituted or unsubstituted alkyl group, an oligooxyethylene group having a repeating number v of an oxyethylene unit of 2 or more, an oligosiloxane group having 2 or more silicon atoms, or a substituted or unsubstituted trialkylsilyl group, provided that the substituted or unsubstituted alkyl group represented by R has a number of carbon atoms in the main chain thereof of 3 or more in the case where L represents a divalent linking group represented by the formula (L-1), 2 or more in the case where L represents a divalent linking group represented by the formula (L-2) or (L-3), or 4 or more in the case where L represents a divalent linking group represented by any one of the formulae (L-4) to (L-12), and R represents a substituted or unsubstituted trialkylsilyl group only in the case where L adjacent to R represents a divalent linking group represented by the formula (L-3):

(L-1)
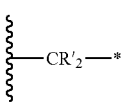

(L-2)
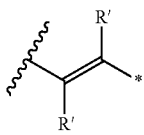

(L-3)
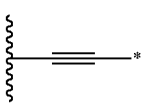

(L-4)
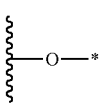

(L-5)
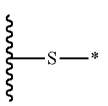

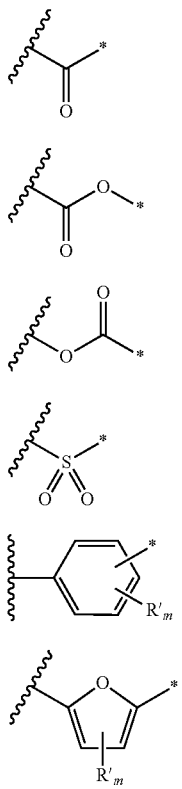
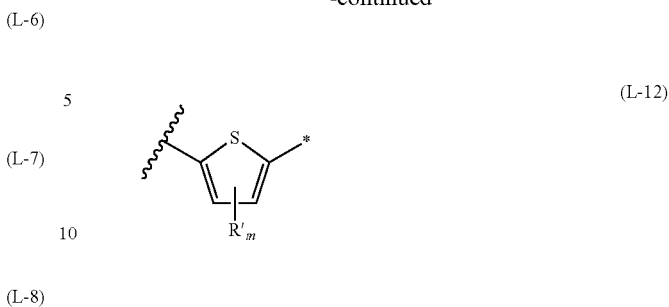

wherein in the formulae (L-1) to (L-12), the wavy line represents a position bonded to the naphthothiazole or naphthoxazole skeleton; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

23. The organic semiconductor thin film for a non-light emitting organic semiconductor device according to claim 22, containing the compound represented by the formula (1-1) or (1-2) and a polymer binder.

24. The organic semiconductor thin film for a non-light emitting organic semiconductor device according to claim 22, which is produced by a solution coating method.

* * * * *